US010618914B2

(12) United States Patent
Huryn et al.

(10) Patent No.: US 10,618,914 B2
(45) Date of Patent: Apr. 14, 2020

(54) 6-ARYL-7-SUBSTITUTED-3-(1H-PYRAZOL-5-YL)-7H-[1,2,4]TRIAZOLO[3,4-B][1,3,4]THIADIAZINES AS INHIBITORS OF THE STAT3 PATHWAY WITH ANTI-PROLIFERATIVE ACTIVITY

(71) Applicant: UNIVERSITY OF PITTSBURGH—OF THE COMMONWEALTH SYSTEM OF HIGHER EDUCATION, Pittsburgh, PA (US)

(72) Inventors: Donna M. Huryn, Allentown, PA (US); Peter Wipf, Pittsburgh, PA (US); Jennifer Rubin Grandis, Pittsburgh, PA (US); Matthew G. LaPorte, Pittsburgh, PA (US); Paul A. Johnston, Sewickley, PA (US); Mark E. Schurdak, Pittsburgh, PA (US); Raffaele Colombo, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/543,573

(22) PCT Filed: Jan. 15, 2016

(86) PCT No.: PCT/US2016/013584
§ 371 (c)(1),
(2) Date: Jul. 13, 2017

(87) PCT Pub. No.: WO2016/115455
PCT Pub. Date: Jul. 21, 2016

(65) Prior Publication Data
US 2019/0100535 A1    Apr. 4, 2019

Related U.S. Application Data

(60) Provisional application No. 62/103,976, filed on Jan. 15, 2015.

(51) Int. Cl.
C07D 513/04    (2006.01)
A61P 35/00    (2006.01)

(52) U.S. Cl.
CPC ............ *C07D 513/04* (2013.01); *A61P 35/00* (2018.01)

(58) Field of Classification Search
CPC ..................... A61P 35/00; C07D 513/04
See application file for complete search history.

(56) References Cited

FOREIGN PATENT DOCUMENTS

WO    WO 2008/011045 A2    1/2008
WO    WO 2008/060578 A2    5/2008

OTHER PUBLICATIONS

LaPorte, et al., Optimization of Pyrazole-containing 1,2,4-triazolo-[3,4-b]thiadiazines, a New Class of STAT3 Pathway Inhibitors, Bioorganic & Medicinal Chemistry Letters 26, 3581-3585 (2016). (Year: 2016).*
Bromberg et al., *The Role of STATs in Transcriptional Control and their Impact on Cellular Function*, Oncogene, 19: 2468-2473 (2000).
Song et al., *STAT Signaling in Head and Neck Cancer*, Oncogene, 19: 2489-2495 (2000).
Garcia et al., *Constitutive Activation of STAT3 in Fibroblasts Transformed By Diverse Oncoproteins and in Breast Carcinoma Cells*, Cell Growth Duff., 812: 1267-76 (1997).
Schaefer et al., *Constitutive Activation of STAT3 in Brain Tumors: Localization to Tumor Endothelial Cells and Activation by the Endothelial Tyrosine Kinase Receptor (VEGFR-2)*, Oncogene, 21: 2058-2065 (2002).
Dhir et al., *STAT3 Activation in Prostatic Carcinomas*, Prostate, 51: 241-246 (2002).
Seki et al., *STAT3 and MAPK in Human Lung Cancer Tissues and Suppression Of Oncogenic Growth by JAB and Dominant Negative STAT3*, Int. J. Oncology, 24: 931-934 (2004).
Huang et al., *Constitutive Activation of STAT3 Oncogene Product in Human Ovarian Carcinoma Cells*, Gynecol. Oncol., 79: 67-73 (2000).
Scholz et al., *Activated Signal Transducer and Activator of Transcription 3 (STAT3) Supports the Malignant Phenotype of Human Pancreatic Cancer*, Gastroenterology, 125: 891-905 (2003).
Benekti et al., *Signal Transducer and Activator of Transcription Proteins in Leukemias*, Blood, 101: 2940-2954 (2003).
Weber-Nordt et al., *Constitutive Activation of STAT Proteins in Primary Lymphoid and Myeloid Leukemia Cells and in Epstein-Barr Virus (EBV)-Related Lymphoma Cell Lines*, Blood, 88: 809-816 (1996).
Bowman et al., *STATs In Oncogenesis*, Oncogene, 19: 2474-2488 (2000).
Yu, H.; Jove, R. *The STATs of cancer—new molecular targets come of age*, Nat. Rev. Cancer, 4: 97-105, (2004).
Wu et al., "Synthesis, structure-activity relationship, and pharmacophore modeling studies of pyrazole-3-carbohydrazone derivatives as dipeptidyl peptidase IV inhibitors," Chem. Biol. Drug. Des., vol. 79, No. 6, pp. 897-906 (2012).
Farag et al., "Synthesis and Structure-Activity Relationship Studies of Pyrazole-based heterocycles as Antitumor Agents," Arch. Pharm. Chem. Life Sci., vol. 343, pp. 384-396 (2010).
International Search Report and Written Opinion issued in related International Patent Application No. PCT/JP2016/013584, dated Aug. 19, 2016.
International Preliminary Report on Patentability issued in related International Patent Application No. PCT/US2016/013584, dated Aug. 19, 2016.

* cited by examiner

*Primary Examiner* — Erich A Leeser
(74) *Attorney, Agent, or Firm* — Foley & Lardner LLP

(57) ABSTRACT

Compounds that selectivity inhibit the STAT3 pathway and not the STAT1 pathway and exhibit anti-proliferative activity are disclosed. Also disclosed are methods of treatment of cancers that are characterized by overexpression of STAT3, which are safer that other therapies.

18 Claims, 6 Drawing Sheets

Figure 2

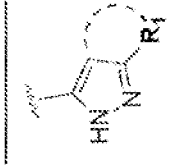
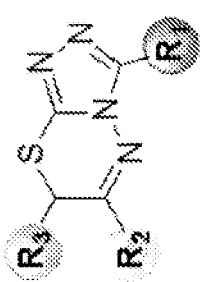

R₁:
Pyrazole: Required
c-Pent fused, X-aryl: Preferred
Inactive: Phenyl, thiophene, pyridyl, benzyl, alkyl, etc.

R₂:
Monosubstitution: improves potency and metabolic stability
Alkyl substitutions (Et, i-Pr, Bn): Tolerated
Polar functionalities (amides, esters): Tolerated Disubstitution: Not tolerated

R₃:
X-aryl: Preferred, diverse aryl substitution tolerated
X-aryl: p-MeOPh, p-ClPh: increase GI activity
Not tolerated: H, alkyl, cycloalkyl, NC-aryl, pyridyl Required: bicyclic system

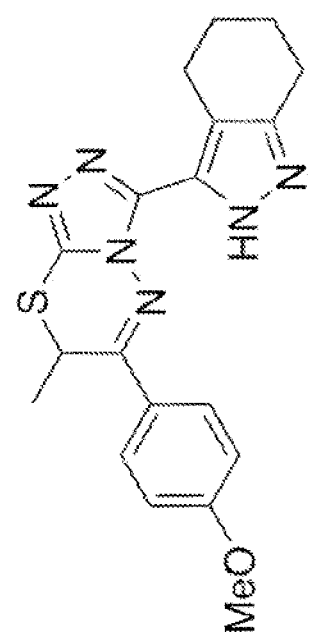
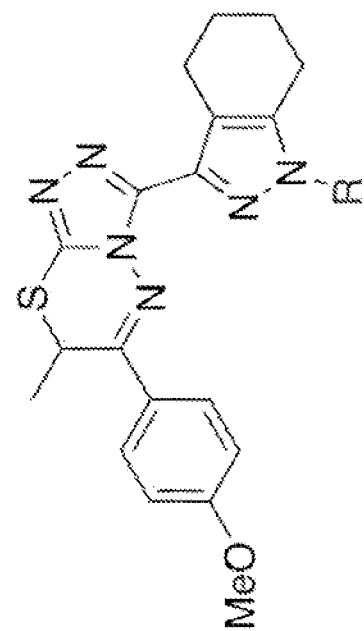
Figure 5

6-ARYL-7-SUBSTITUTED-3-(1H-PYRAZOL-5-YL)-7H-[1,2,4]TRIAZOLO[3,4-B][1,3,4]THIADIAZINES AS INHIBITORS OF THE STAT3 PATHWAY WITH ANTI-PROLIFERATIVE ACTIVITY

CROSS REFERENCE TO RELATED APPLICATIONS

This application is the National Phase of International Patent Application No. PCT/US2016/013584, filed Jan. 15, 2016, which claims priority from U.S. Provisional Patent Application No. 62/103,976, filed Jan. 15, 2015. The contents of these applications are incorporated herein by reference in their entirety.

STATEMENT OF GOVERNMENT SUPPORT

This invention was made with government support under #HHSN261200800001E awarded by the NIH. The government has certain rights in the invention

BACKGROUND

Signal transducer and activator of transcription 3 ("STAT3") is a member of the STAT family of transcription factors that relate signals from extracellular signaling protein receptors on the plasma membrane directly to the nucleus. See e.g., Bromberg et al., *The Role of STATs in Transcriptional Control and their Impact on Cellular Function, Oncogene*, 19: 2468-2473 (2000).

STAT3 has been shown to be constitutively activated in cancer including, but not limited to, cancers of the brain, head, neck, breast, prostate, lung, ovary, pancreas, leukemia, multiple myeloma, and lymphoma. See e.g., Song et al., *STAT Signaling in Head and Neck Cancer, Oncogene*, 19: 2489-2495 (2000); Garcia et al., *Constitutive Activation of STAT3 in Fibroblasts Transformed By Diverse Oncoproteins and in Breast Carcinoma Cells, Cell Growth Duff.*, 812: 1267-76 (1997); Schaefer et al., *Constitutive Activation of STAT3 in Brain Tumors: Localization to Tumor Endothelial Cells and Activation by the Endothelial Tyrosine Kinase Receptor (VEGFR-2), Oncogene*, 21: 2058-2065 (2002); Dhir et al., *STAT3 Activation in Prostatic Carcinomas*, Prostate, 51: 241-246 (2002); Seki et al., *STAT3 and MAPK in Human Lung Cancer Tissues and Suppression Of Oncogenic Growth by JAB and Dominant Negative STAT3, Int. J. Oncology*, 24: 931-934 (2004); Huang et al., *Constitutive Activation of STAT3 Oncogene Product in Human Ovarian Carcinoma Cells, Gynecol. Oncol.*, 79: 67-73 (2000); Scholz et al., *Activated Signal Transducer and Activator of Transcription 3 (STAT3) Supports the Malignant Phenotype of Human Pancreatic Cancer, Gastroenterology*, 125: 891-905 (2003); Benekti et al., *Signal Transducer and Activator of Transcription Proteins in Leukemias, Blood*, 101: 2940-2954 (2003); Weber-Nordt et al., *Constitutive Activation of STAT Proteins in Primary Lymphoid and Myeloid Leukemia Cells and in Epstein-Barr Virus (EBV)-Related Lymphoma Cell Lines, Blood*, 88: 809-816 (1996); Bowman et al., *STATs In Oncogenesis*, Oncogene, 19: 2474-2488 (2000); Yu, H.; Jove, R. *The STATs of cancer—new molecular targets come of age, Nat. Rev. Cancer*, 4: 97-105, (2004).

Small molecules have been developed that inhibit the STAT3 pathway; however, there remains a need for compounds that selectivity inhibit the STAT3 pathway and not the STAT1 pathway and which exhibit anti-proliferative activity. Furthermore, there is a need for compounds that demonstrate improved, potency, solubility and/or stability. The present invention satisfies these needs.

SUMMARY OF THE DISCLOSED SUBJECT MATTER

One embodiment of the invention relates to a compound represented by the following formula:

wherein:
R is selected from the group consisting of a $C_1$-$C_6$ alkyl or aryl, optionally substituted by one or
more selected from the group consisting of —OR', —NR'R",

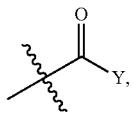

and an optionally substituted phenyl, wherein
(1) R' and R" are each independently selected from —H, $C_1$-$C_6$ alkyl, and $C_1$-$C_6$ alkyl substituted by one or more fluro groups, and when R' and R" are each alkyl they may form a ring,
(2) Y is selected from $C_1$-$C_6$ alkyl, —OR', and —NR'R", wherein when the optionally substituted phenyl contains a substituent, the substituent is selected from —OR', —NR'R", and

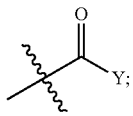

$R_1$ is

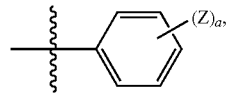

wherein
(1) each Z is independently selected from halogen, $C_1$-$C_6$ alkyl, $C_1$-$C_6$ alkyl substituted by one or more fluro groups, —OR', —NR'R",

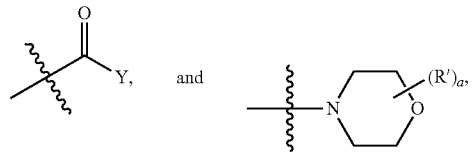

(2) a is an integer of 0 to 4,
(3) Y' is selected from $C_1$-$C_6$ alkyl, $C_1$-$C_6$ alkyl substituted by one or more fluoro groups, —OR', and —NR'R", wherein R and $R_1$ may form a ring;
X is

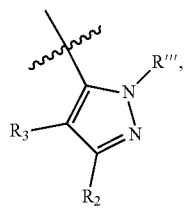

phenyl optionally substituted by one or more halogen,

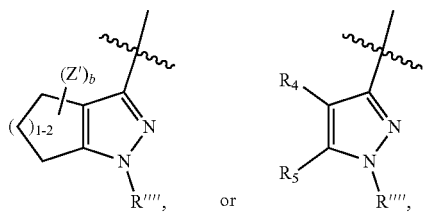

wherein
(1) $R_2$ is phenyl optionally substituted by one or more halogen and $R_3$ is hydrogen or a halogen, or $R_2$ and $R_3$ form a 5 or 6-membered ring comprising $sp^3$ carbon atoms, and optionally one heteroatom selected from S, NR* and O, wherein R* is H, $C_1$-$C_6$ alkyl or benzyl,
(2) $R_5$ is phenyl optionally substituted by one or more halogen and $R_4$ is hydrogen or a halogen, or $R_5$ and $R_4$ form a 5 or 6-membered ring comprising carbon atoms, and optionally one heteroatom selected from S, NR* and O, wherein R* is H, $C_1$-$C_6$ alkyl or benzyl,
(3) Z' is halogen, benzyl, $C_1$-$C_6$ alkyl, and $C_1$-$C_6$ alkyl substituted by one or more fluoro groups,
(4) b is an integer from 0 to 4,
(5) R''' is hydrogen, $C_1$-$C_6$ alkyl, benzyl,

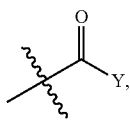

wherein the benzyl may be substituted by one or more halogen, $C_1$-$C_6$ alkyl, or $C_1$-$C_6$ alkyl substituted by one or more fluoro groups —OR',
(6) R'''' is hydrogen, $C_1$-$C_6$ alkyl, benzyl, or

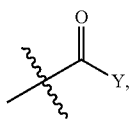

wherein the benzyl may be substituted by one or more halogen, $C_1$-$C_6$ alkyl, or $C_1$-$C_6$ alkyl substituted by one or more fluoro groups —OR', or a pharmaceutically acceptable salt thereof, and wherein when R and $R_1$ are both unsubstituted phenyl, then $R_2$ cannot be unsubstituted phenyl.

In another embodiment, R and $R_1$ form a 5 or 6 membered ring that is optionally substituted by one or more selected from the group consisting of —OR', —NR'R",

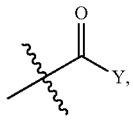

and an optionally substituted phenyl. In yet another embodiment, for $R_1$, a is 1 or 2, and Z is independently selected from fluoro, chloro, methyl, methoxy, and trifluoromethyl.

In yet another embodiment, X is

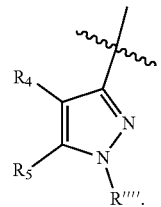

In yet another embodiment, X is

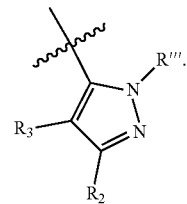

In yet another embodiment, $R_2$ and $R_3$ form a 5 or 6-membered ring comprising $sp^3$ carbon atoms, and optionally one heteroatom selected from S, NR* and O.

In yet another embodiment, the compound is represented by one of the formulae in Table 1.

Another embodiment of the invention relates to a pharmaceutical formulation comprising a compound according to any of the preceding embodiments and at least one pharmaceutically acceptable excipient.

Another embodiment of the invention relates to a method of treating a Squamous Cell Carcinoma in a patent in need thereof, comprising administering to the patient a therapeutically effective amount of a compound according to any one of the preceding embodiments or a pharmaceutical formulation according to any one of the preceding embodiments. In yet another embodiment, the Squamous Cell Carcinoma is located in the head and/or neck.

Another embodiment of the invention is directed to a method of treating a cancer with hyper-activated STAT3 in a patent in need thereof. The method comprises administering to the patient a therapeutically effective amount of a compound according to any one of the preceding embodiments or a pharmaceutical formulation according to any one of the preceding embodiments.

Another embodiment of the invention is directed to a method of inhibiting STAT3 comprising contacting STAT3 with a compound according to any one of the preceding embodiments or a pharmaceutical formulation according to any one of the preceding embodiments.

Yet another embodiment of the invention is directed to a method of selectively inhibiting STAT3 in the presence of STAT1 comprising contacting STAT3 with a compound according to any one of the preceding embodiments or a pharmaceutical formulation according to any one of the preceding embodiments.

Another embodiment of the invention is directed to a method of treatment of a STAT3-mediated disease comprising the administration of a therapeutically effective amount of a compound according to any one of the preceding embodiments or a pharmaceutical formulation according to any one of the preceding embodiments to a patient in need thereof.

In yet another embodiment, the disease is cancer, for example, the cancer is Squamous Cell Carcinoma.

In the methods of the invention, the compound or composition can be administered via any pharmaceutically acceptable method, including but not limited to oral administration.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 2 shows a SAR summary.

FIG. 5 shows a scheme for pyrazole substitution.

DETAILED DESCRIPTION

I. Compounds of the Invention

Figure 1:
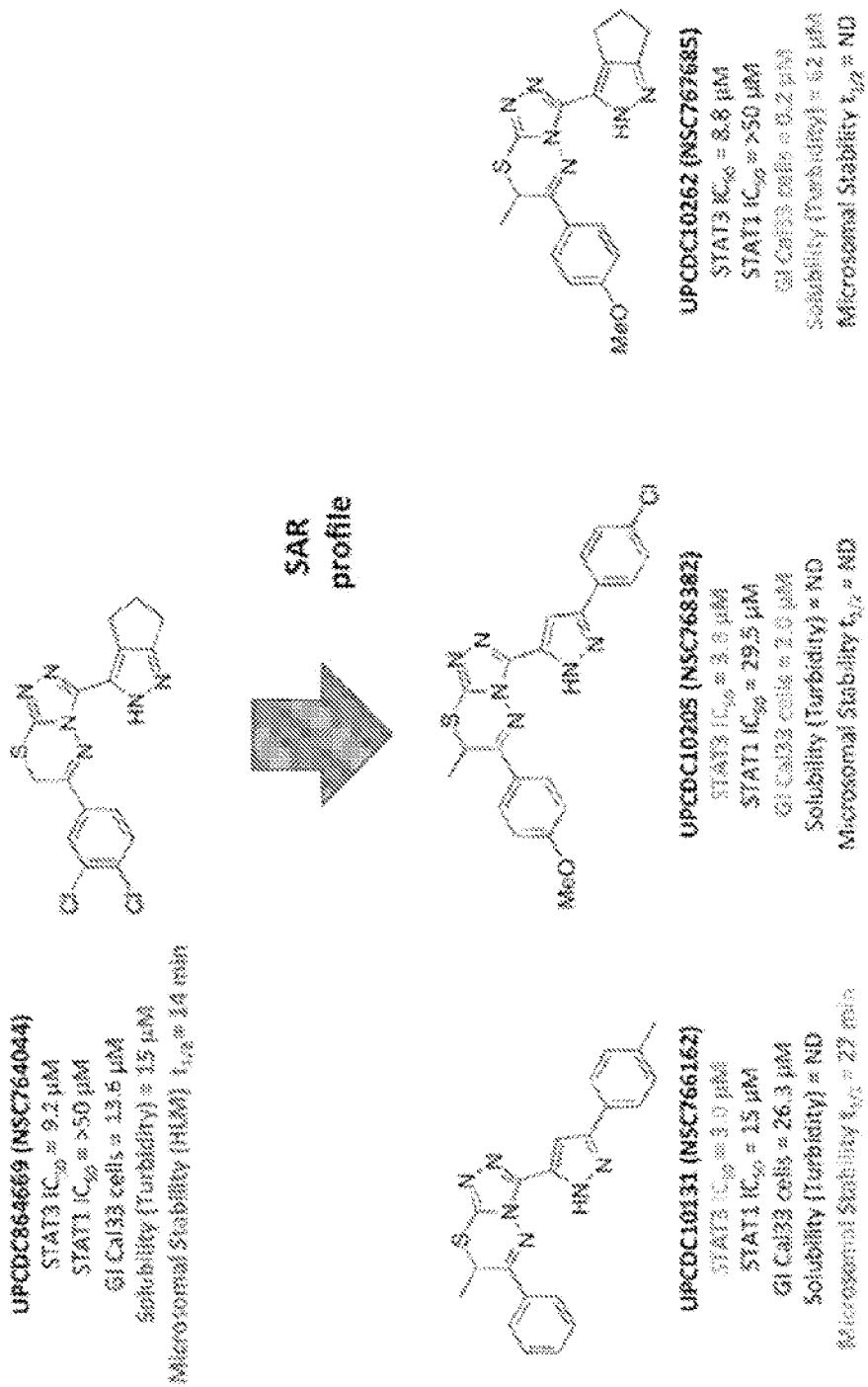
FIG. 1 shows an embodiment of representative structure activity relationships ("SAR") improvements.

Compounds of the present disclosure include novel compounds with the following core structure:

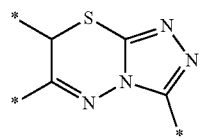 [SMILES: *C1=Nn2c(*)nnc2SC1*]

The core structure is substituted at one or more position marked as *.

In some embodiments, the compounds of the present disclosure are represented by the following structure:

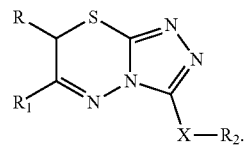

In Compound (I), R is preferably a substituent other than hydrogen, and optionally a substituted alkyl or aryl; $R_1$ is an optionally substituted aryl and X is an optionally substituted pyrazole or benzyl. In some embodiments, the "R" alpha-position is not di-substituted. In some embodiments, $R_1$ is aryl or halogenated-aryl.

In one embodiment, R is selected from the group consisting of a $C_1$-$C_6$ alkyl or aryl, optionally substituted by one or more selected from the group consisting of —OR', —NR'R",

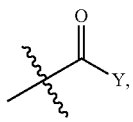

and an optionally substituted phenyl, wherein: (1) R' and R" are each independently selected from —H, $C_1$-$C_6$ alkyl and $C_1$-$C_6$ alkyl substituted by one or more fluro groups, and when R' and R" are each alkyl they may form a ring, (2) Y is selected from $C_1$-$C_6$ alkyl, —OR', and —NR'R", and (3) when the optionally substituted phenyl contains a substituent, the substituent is
selected from —OR', —NR'R", and

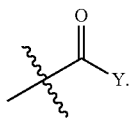

In another embodiment, R is a $C_1$-$C_6$ alkyl or a benzyl. In yet another embodiment, R is selected from the group consisting of Me, Et, iPr, iBu, and Bn. In another embodiment, R is selected from the group consisting of substituted benzyl, wherein the benzyl is substituted by $C_1$-$C_6$ alkyl, $C_1$-$C_6$ alkyl substituted by one or more fluro groups, —OR', —NR'R", or

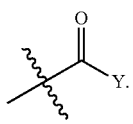

In another embodiment, $R_1$ is

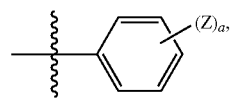

wherein each Z is independently selected from halogen, $C_1$-$C_6$ alkyl, $C_1$-$C_6$ alkyl substituted by one or more fluro groups, —OR', —NR'R", and

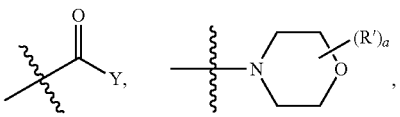

where a is an integer of 0 to 4, Y' is selected from $C_1$-$C_6$ alkyl, $C_1$-$C_6$ alkyl substituted by one or more fluro groups, —OR', and —NR'R". Substituents, such as R' and R", which are not explicitly defined, are selected from the same moieties as those listed above for R. In some embodiments, a is 0, 1, 2, 3 or 4.

In another embodiment, R and $R^1$ form a ring. For example, R and $R^1$ can form a 5 or 6-membered cycloalkyl, which may be optionally substituted by one or more $C_1$-$C_6$ alkyl, $C_1$-$C_6$ alkyl substituted by one or more fluro groups, —OR', —NR'R", or

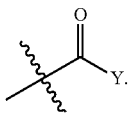

In another embodiment, R and $R^1$ form a 5 or 6 membered ring that is optionally substituted by one or more selected from the group consisting of —OR', —NR'R",

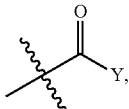

and an optionally substituted phenyl.

In one embodiment, X is

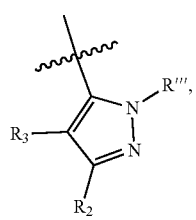

phenyl optionally substituted by one or more halogen,

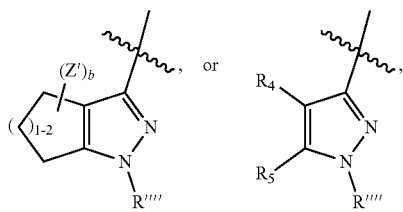

wherein (1) $R_2$ is phenyl optionally substituted by one or more halogen and $R_3$ is hydrogen or a halogen, (2) $R_2$ and $R_3$ form a 5 or 6-membered ring comprising $sp^3$ carbon atoms, and optionally one heteroatom selected from S, NR* and O, wherein R* is H, $C_1$-$C_6$ alkyl or benzyl; (3) $R_5$ is phenyl optionally substituted by one or more halogen, and $R_4$ is hydrogen or a halogen, (4) $R_5$ and $R_4$ form a 5 or 6-membered ring comprising carbon atoms, and optionally one heteroatom selected from S, NR* and O, wherein R* is H, $C_1$-$C_6$ alkyl or benzyl, (5) Z' is halogen, benzyl, $C_1$-$C_6$ alkyl, $C_1$-$C_6$ alkyl substituted by one or more fluro groups; (6) b is an integer from 0 to 4; (7) R'" is hydrogen, $C_1$-$C_6$ alkyl, benzyl, or

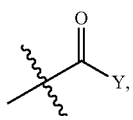

wherein the benzyl may be substituted by one or more halogen, $C_1$-$C_6$ alkyl, or $C_1$-$C_6$ alkyl substituted by one or more fluro groups —OR'; (8) R"" is hydrogen, $C_1$-$C_6$ alkyl, benzyl, or

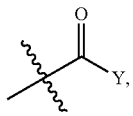

wherein the benzyl may be substituted by one or more halogen, $C_1$-$C_6$ alkyl, $C_1$-$C_6$ alkyl substituted by one or more fluro groups —OR', or a pharmaceutically acceptable solvate or salt thereof, wherein when R and $R_1$ are both unsubstituted phenyl, then $R_2$ cannot be unsubstituted phenyl. In the above embodiments, wherein when R and $R^1$ are both unsubstituted phenyl, then $R^2$ cannot be unsubstituted phenyl.

In some embodiments, when $R_2$ and $R_3$ form a 5 or 6-membered ring, the ring comprises one or more $sp^3$ carbon atoms, and optionally one heteroatom selected from S, NR* and O. Additional exemplary compounds are shown in the examples; e.g., in Table 2.

II. Methods of Treatment

One aspect of the present technology includes methods of inhibiting STAT3 comprising contacting STAT3 with a compound or composition of the present disclosure. In some embodiments, the methods include selectively inhibiting STAT3 in the presence of STAT1 comprising contacting STAT3 with a compound or composition of the present disclosure.

Another aspect of the present technology includes methods of treatment of a STAT3-mediated disease comprising the administration of a therapeutically effective amount of a compound or composition of the present disclosure. The STAT3-mediated disease may be, for example, a cancer, such as, a cancer known to have hyper-activated STAT3. As noted above, STAT3 has been shown to be constitutively activated in cancer including, but not limited to, cancers of the brain, head, neck, breast, prostate, lung, ovary, pancreas, leukemia, multiple myeloma, and lymphoma.

Accordingly, an aspect of the present invention includes methods of treating cancers with hyper-activated signal transducer and activator of transcription 3 ("STAT3") in a subject diagnosed as having, suspected as having, or at risk of having cancers with hyper-activated STAT3, such as for example Squamous Cell Carcinoma ("SCC") or other types of cancers described herein. As such, some embodiments of the invention include methods of treating a subject in need thereof who is suffering from, suspected as having, or at risk of having SCC. In some embodiments, the SCC is located in the head and/or neck. In some embodiments, the treatment of the subject in need thereof comprises administering a compound of the present disclosure to the subject suspected of, or already suffering from SCC, such as, e.g., aberrant levels and/or function of genes involved in squamous cell carcinogenesis compared to a normal control subject, or SCC, in an amount sufficient to cure, or at least partially arrest, the symptoms of the disease, including its complications and intermediate pathological phenotypes in development of the disease.

The compound of the present disclosure may be included in a pharmaceutical formulation, such as those disclosed herein, and may be administered in any pharmaceutically acceptable manner, including methods of administration described herein.

In another aspect of the invention, a compound of the present disclosure is administered in an amount sufficient to provide improved selectivity, potency, solubility and/or stability over prior art compounds, for example, a compound of the present disclosure improves STAT3 potency while maintaining selectivity over STAT1 and/or improves growth inhibition (GI) potency and/or increases solubility, and/or increases microsomal stability. In some embodiments, the improved selectivity, potency, solubility and/or stability is in comparison to a non-alpha-substituted compound, such as:

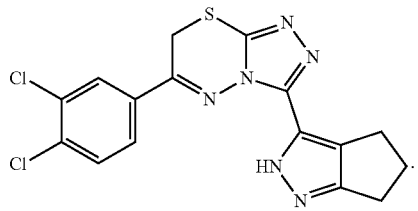 [SMILES: Clc1ccc(C2=Nn3c(nnc3-c3[nH]nc4c3CCC4)SC2)cc1Cl]

In other embodiments, the STAT3 $IC_{50}$ is about <20 µM and the STAT3 $IC_{50}$ is more than or equal to about 3-fold less than STAT1 $IC_{50}$, and the GI50 is about <20 µM. For example, in some embodiments, the $IC_{50}$ is about <20 µM and the STAT3 $IC_{50}$ is about 3- to about 20-fold, or about 3- to about 10-fold less than STAT1 $IC_{50}$.

The compound useful in the methods of the present technology is administered to a mammal in an amount effective in treating or preventing SCC. The therapeutically effective amount can be determined by methods known in the art.

An effective amount of a compound useful in the methods of the present technology, for example in a pharmaceutical composition, may be administered to a mammal in need thereof by any of a number of well-known methods for administering pharmaceutical compounds. The compound may be administered systemically or locally. In one embodiment, the compound is administered intravenously. For example, the compounds useful in the methods of the present technology may be administered via rapid intravenous bolus injection. In some embodiments, the compound is administered as a constant rate intravenous infusion. The compound may also be administered orally, topically, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord. In another embodiment, the compound is administered orally, for example, in the form of a tablet, push-fit capsule, soft, sealed capsule and the like.

The compounds useful in the methods of the present technology may also be administered to mammals by sustained release, as is known in the art. Sustained release administration is a method of drug delivery to achieve a certain level of the drug over a particular period of time. The level typically is measured by serum or plasma concentration.

III. Pharmaceutical Formulations

For oral administration, liquid or solid formulations may be used. Some examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present technology may utilize conventional diluents, carriers, or excipients etc., such as are known in the art can be employed to deliver the compounds. For example, the formulations may comprise one or more of the following: a stabilizer, a surfactant, such as a nonionic surfactant, and optionally a salt and/or a buffering agent. The compound may be delivered in the form of a solution, or in a lyophilized form.

In some embodiments, the stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. In some embodiments, the stabilizer or combination of stabilizers constitutes from about 0.1% to about 10% weight for weight of the compound.

In some embodiments, the surfactant is a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally contain one or more conventional additives. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In one embodiment, the mammal is a human.

In some embodiments, the compounds of the invention are administered orally or via injection at a dose of from about 0.1 to about 500 mg/kg per day, or at any dosage in between these quantities (e.g., about 5, about 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 225, about 250, about 275, about 300, about 325, about 350, about 375, about 400, about 425, about 450, about 475, or about 500 mg/kg per day.

The dose range for adult humans may be generally from about 5 mg to about 2 g/day (e.g., about 5 mg to about 2000 mg/day). For example, the dose range for an adult human can be about 5, about 10, about 15, about 20, about 25, about 50, about 75, about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, or about 2000 mg/day.

Administration may be in single or multiple daily doses, or any other desired dosage frequency such as every other day, 2 or more times a week, 1x week, etc. In other embodiments, the compound or composition can be administered once daily, twice daily or three times daily. It is to be understood that precise amounts of the compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated.

IV. Combination Therapy

In some embodiments, the compounds of the present disclosure may be combined with one or more additional therapies for the prevention or treatment of a STAT3-mediated disease, such as cancers with hyper-activated STAT3, e.g., SCC or other cancers as described herein. It is an aspect of this invention that a compound or composition of the invention is used in combination with another agent or therapy method, such as another cancer treatment. The administration of the compound or composition of the invention may be concurrent, or may precede or follow the other agent treatment by intervals ranging from minutes to weeks, for example. Additional therapeutic agents or active agents include, but are not limited to, alkylating agents, nitrosoureas, antimetabolites, antitumor antibiotics, plant *vinca* alkaloids, and steroid hormones.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Additional combination therapies include, but are not limited to chemotherapy, radiotherapy, radiochemotherapy, immunotherapy, gene therapy and/or surgery.

In specific embodiments, the additional therapy also targets cancers with hyper-activated STAT3, e.g., SCC or other cancers as described herein. Combination chemotherapy include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, COX-2 inhibitors, cholesterol synthesis inhibitors, cisplatinum, 5-fluorouracil, vincristin, vinblastin, staurosporine, streptozocin, fludurabine, methotrexate, genistein, curcumin, resveratrol, silymarin, caffeic acid phenethyl ester, flavopiridol, emodin, green tea polyphenols, piperine, oleandrin, ursolic acid, butamic acid, actinomycin D, thalidomide or any analog or derivative variant of the foregoing. Chemotherapy can be systemic, targeted and/or hormonal based. These can be used individually or in combination. Exemplary breast cancer therapy includes herceptin, tykerb, arastin, tamoxifen, and aromatic inhibitors. Other exemplary treatments are oxaliplatin, docetaxel, imatinib, and abraxan, in addition to tyrosine kinase inhibitors such as sorefinib or sunitinib. One of skill in the art would know that siRNA types of cancer treatment may also be considered.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Radiochemotherapy is the combined delivery of radiation and chemotherapy to a target. This can be achieved in a single agent through conjugation of a chemotherapeutic agent to a chelating moiety, which is then subsequently radiolabeled with a therapeutic radionuclide. Combinations of radiochemotherapy include, for example, cisplatin (CDDP) with a-emitters, cyclophosphamide with b-emitters, doxorubicin with b/g-emitters and taxol with Auger-emitters, or any analog or derivative variant of the foregoing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, possibly in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155, for example.

In yet another embodiment, the secondary treatment is a gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues, in certain cases.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically or partially removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue. Breast cancer surgery includes mastectomy or lumpectomy.

V. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

VI. Working Examples

The present technology is further illustrated by the following examples, which should not be construed as limiting in any way.

General Information.

All moisture and air-sensitive reactions were performed using syringe-septum cap techniques under an inert atmosphere ($N_2$ or Ar) in glassware that was dried in an oven at 140° C. for at least 2 h prior to use. Reactions carried out at a temperature below 0° C. employed a $CO_2$/acetone bath. All reagents and solvents were used as received unless otherwise specified.

Triethylamine, N,N-dimethylaniline, and pyridine were distilled over $CaH_2$. THF and $Et_2O$ were distilled over sodium/benzophenone ketyl. DCM and toluene were purified using an alumina column filtration system. Anhydrous MeOH and $Et_2O$ were purchased from Acros Organics and Fisher Scientific, respectively. Anhydrous DMF was purchased from Acros Organics or distilled and stored over 4 Å molecular sieves. Analytical thin-layer chromatography (TLC) was performed on pre-coated $SiO_2$ 60 F254 plates (250 μm layer thickness) available from Merck. Visualization was accomplished by UV irradiation at 254 nm and/or by staining with Vaughn's reagent (4.8 g $(NH_4)_6Mo_7O_{24}.4H_2O$ and 0.2 g $Ce(SO_4)_2.4H_2O$ in 100 mL of a 3.5 N $H_2SO_4$ solution), a $KMnO_4$ solution (1.5 g $KMnO_4$ and 1.5 g $K_2CO_3$ in 100 mL of a 0.1% NaOH solution), a ninhydrin solution (2 g ninhydrin in 100 mL EtOH), a PMA solution (5 g phosphomolybdic acid in 100 mL EtOH), or a p-anisaldehyde solution (2.5 mL p-anisaldehyde, 2 mL AcOH and 3.5 mL conc. aq. $H_2SO4$ in 100 mL EtOH). Preparative thin-layer chromatography was performed on pre-coated $SiO_2$ GF ($UV_{254}$) 1000 microns (20×20 cm) plates available from Analtech. Flash column chromatography was performed using $SiO_2$ 60 (particle size 0.040-0.055 mm, 230-400 mesh, or Silicycle SiliaFlash® P60, 40-63 m). Melting points were determined on a Mel-Temp capillary melting point apparatus fitted with a Fluke 51 II digital thermometer. Infrared spectra were recorded on a Smiths IdentifyIR ATR spectrometer or a Perkin Elmer Spectrum 100 FT-IR spectrometer using the Universal ATR Sampling Accessory for both oil and solid compounds. $^1$H NMR and $^{13}$C NMR spectra were obtained on a Bruker Avance 300, 400, 500, or 600 instrument at 300/75 MHz, 400/100 MHz, 500/125 MHz, or 600/150 MHz, respectively. Chemical shifts were reported in parts per million (ppm) as referenced to residual solvent. $^1$H NMR spectra are tabulated as follows: chemical shift, multiplicity (app=apparent, br=broad, s=singlet, d=doublet, t=triplet, q=quartet, quint=quintuplet, sext, =sextuplet, m=multiplet), coupling constant(s), number of protons. $^{13}$C NMR were obtained using a proton-decoupled pulse sequence and are tabulated by observed peak.

Example 1

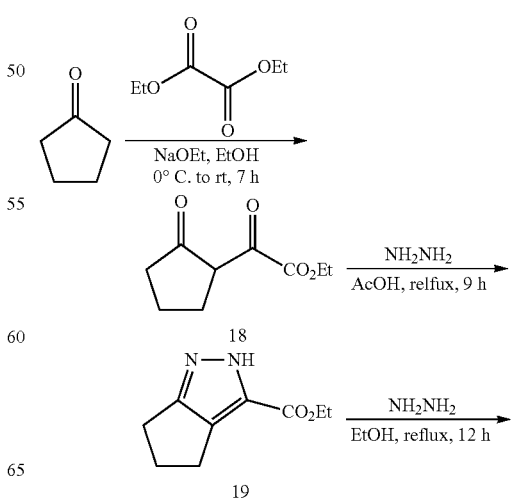

Scheme. Synthesis of UPCDC 864669

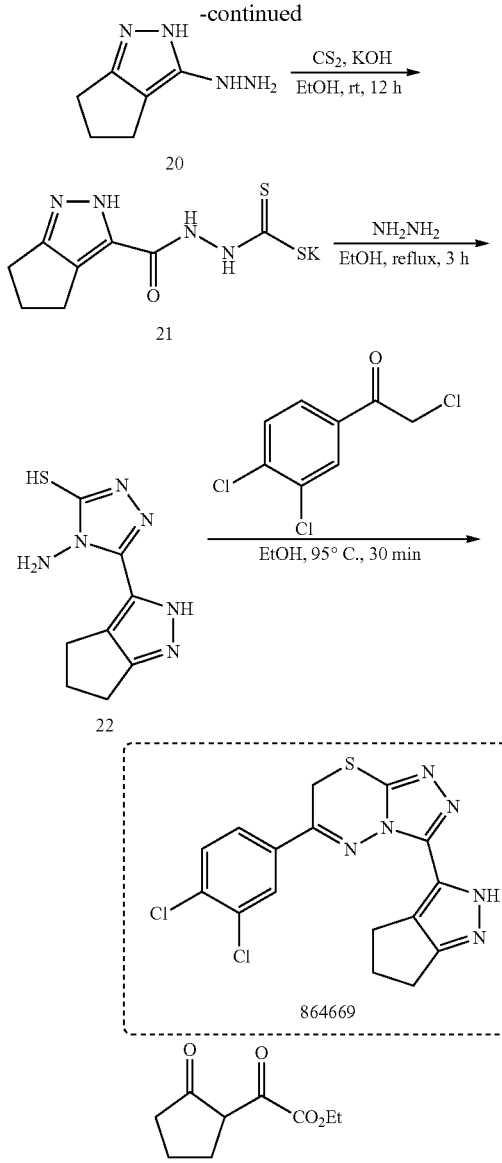

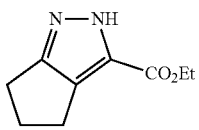 [SMILES: CCOC(=O)c1[nH]nc2c1CCC2]

Ethyl 2,4,5,6-tetrahydrocyclopenta[c]pyrazole-3-carboxylate (19).[i]

Hydrazine hydrate (1.20 mL, 24.8 mmol) was slowly added to a solution of 18 (3.80 g, 20.6 mmol) in acetic acid (12 mL) at 0° C. The mixture was heated to reflux for 9 h, cooled to 0° C., and diluted with water. The white precipitate was filtered, dried, and purified by chromatography on silica gel (10% MeOH/DCM) to afford the desired product 19 as a white solid (1.38 g, 37%): $^1$H NMR (400 MHz; CDCl$_3$, 100° C.): δ 4.27 (q, J=7.2 Hz, 2H), 2.72-2.65 (m, 4H), 2.45-2.42 (m, 2H), 1.40 (t, J=7.1 Hz, 3H); HRMS (ESI) m/z calcd for C$_9$H$_{13}$O$_2$N$_2$ [M+H]$^+$ 181.0972, found 181.0971.

[i] Wu et al., *Chem. Biol. Drug. Des.*, 79: 897-906 (2012).

2,4,5,6-Tetrahydrocyclopenta[c]pyrazole-3-carbohydrazide (20).[i]

A mixture of 19 (5.0 g, 28 mmol) and hydrazine hydrate (4.1 mL, 83 mmol) in ethanol (80 mL) was refluxed for 12 h. After cooling, the formed white precipitate was filtered, washed with Et$_2$O, and dried under vacuum to afford 20 as a white solid (4.1 g, 89%). The product was used in the next step without further purification: $^1$H NMR (400 MHz; DMSO-d6, 100° C.): δ 12.3 (br s, 1H), 8.58 (br s, 1H), 4.25 (br s, 2H), 2.71 (t, J=7.1 Hz, 2H), 2.64 (t, J=7.2 Hz, 2H), 2.47-2.42 (m, 2H); HRMS (ESI) m/z calcd for C$_9$H$_{13}$O$_2$N$_2$ 167.0927, found 167.0926. [i] Wu et al., *Chem. Biol. Drug. Des.*, 79: 897-906 (2012).

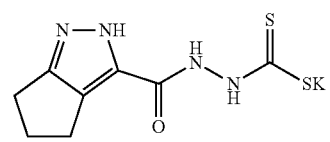

Potassium 2-(2,4,5,6-tetrahydrocyclopenta[c]pyrazole-3-carbonyl)hydrazinecarbodithioate (21)

A solution of KOH (2.0 g, 36 mmol) in EtOH (10 mL) was added to a suspension of 20 (4.0 g, 24 mmol) in EtOH (100 mL). When the suspension became a solution, CS$_2$ (2.2 mL, 36 mmol) was added, the mixture became cloudy, and a precipitate was formed within 1-2 min. The suspension was stirred at rt for 12 h, diluted with ethyl ether (100 mL), and filtered. The filtrate was washed with cold diethyl ether and dried under vacuum to afford the desired product 21 as a white/pale yellow solid (6.4 g, 95%), which was directly used in the next step.

Ethyl 2-oxo-2-(2-oxocyclopentyl)acetate (18).[i]

Sodium (1.3 g, 56.8 mmol) was added to anhydrous ethanol (125 mL) in a three-necked round bottom flask equipped with a reflux condenser under N$_2$ atmosphere. A solution of cyclopentanone (4.6 mL, 51.6 mmol) in diethyl oxalate (7 mL, 51.6 mmol) was cooled to 0° C. prior to its dropwise addition to a prepared solution of sodium ethoxide in EtOH. The ice bath was retained for 1 h, and the reaction mixture was stirred at rt for an additional 6 h. The mixture was poured into ice/water, acidified with 2 M HCl to pH<2, and extracted with DCM (3×). The organic extracts were combined, washed with brine, dried, and evaporated. The crude residue was purified by chromatography on silica gel (EtOAc/hexanes, 1:9) to give the desired product 18 as an oil (4.8 g, 50%): $^1$H NMR (400 MHz, CDCl$_3$) δ 12.94 (br s, 1H), 4.35 (q, J=7.2 Hz, 2H), 2.96 (t, J=7.6 Hz, 2H), 2.48 (t, J=7.6 Hz, 2H), 1.99 (quint, J=7.6 Hz, 2H), 1.38 (t, J=7.2 Hz, 2H). [i] Wu et al., *J. Chem. Biol. Drug. Des.*, 79: 897-906 (2012).

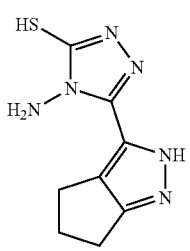

4-Amino-5-(2,4,5,6-tetrahydrocyclopenta[c]pyrazol-3-yl)-4H-1,2,4-triazole-3-thiol (22)

A suspension of 21 (6.4 g, 23 mmol) and hydrazine hydrate (2.2 mL, 46 mmol) in water (20 mL) was refluxed for 3 h. The mixture was diluted with cold water (50 mL) and acidified to pH 4-5 with concentrated HCl, resulting in a white solid precipitate. The solid was filtered, washed with cold water, suspended in EtOH, diluted with diethyl ether, and re-filtered to afford the desired product 22 (2.6 g, 51%) as a white solid: Mp 290° C.; $^1$H NMR (400 MHz; DMSO-$d_6$, 100° C.): δ 13.50 (br s, 1H), 5.75 (br s, 2H), 4.25 (br s, 2H), 2.77 (t, J=7.0 Hz, 2H), 2.72 (t, J=7.0 Hz, 2H), 2.48-2.43 (m, 2H); $^{13}$C NMR (100 MHz; DMSO-$d_6$, 100° C.): δ 164.9, 143.3, 129.0, 127.3, 125.3, 29.5, 23.4, 23.0; IR (ATR, neat) 3267, 3180, 3083, 2930, 2857, 1625, 1523, 1459, 1048, 1025, 714 cm$^{-1}$; HRMS (ESI) m/z calcd for $C_8H_9N_6S$ [M+H]$^+$ 223.0740, found 223.0741.

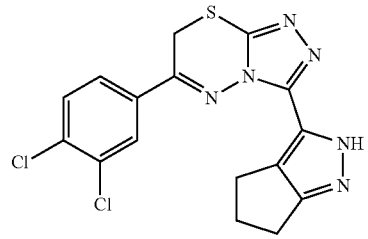 [SMILES: Clc1ccc(C2=Nn3c(nnc3-c3[nH]nc4c3CCC4)SC2)cc1Cl]

6-(3,4-Dichlorophenyl)-3-(2,4,5,6-tetrahydrocyclopenta[c]pyrazol-3-yl)-7H [1,2,4]triazolo[3,4-b][1,3,4]thiadiazine (UPCDC864669).

A solution 21 (0.0250 g, 0.112 mmol) and 2,3',4'-trichloroacetophenone (0.0251 g, 0.112 mmol) in EtOH (1 mL) was heated to 95° C. under microwave-irradiation for 30 min (LC-MS analysis showed that the conversion was completed). The solvent was evaporated, and the crude residue was purified by chromatography on silica gel (10% MeOH/DCM) to afford the desired product UPCDC864669 (0.038 g, 88%) as a white powder: Mp 209° C.; $^1$H NMR (400 MHz, DMSO-$d_6$, 100° C.) δ 8.27 (d, J=2.4 Hz, 1H), 7.99 (dd, J=8.4 Hz, 2.0 Hz, 1H), 7.87 (d, J=8.4 Hz, 1H), 4.45 (s, 2H), 2.73-2.68 (m, 4H), 2.43-2.40 (m, 2H); $^{13}$C NMR (100 MHz, DMSO-$d_6$, 100° C.) δ 153.7, 141.6, 134.0, 132.0, 131.2, 129.4, 127.6, 30.0, 24.0, 23.6, 22.9, 4 quaternary carbons were missing; IR (ATR, neat) 3154, 2902, 1506, 1458, 818 cm$^{-1}$; HRMS (ESI) m/z calcd for $C_{16}H_{13}Cl_2N_6S$ [M+H]$^+$ 391.0294, found 391.0287.

Example 2

General Scheme: General synthesis of alpha-substituted compounds

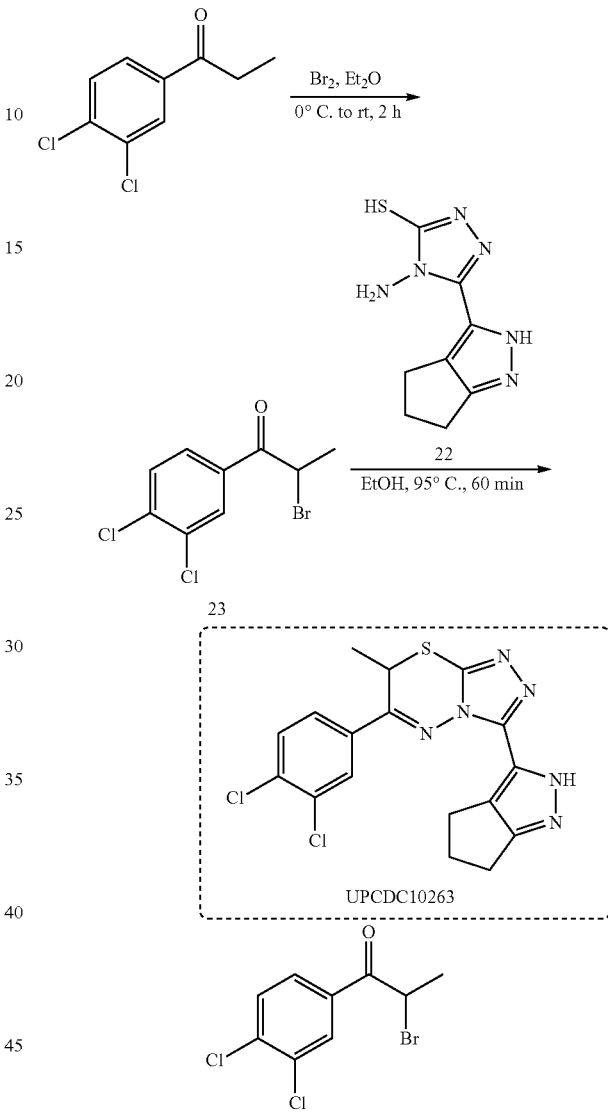

2-Bromo-1-(3,4-dichlorophenyl)propan-1-one (23)

At 0° C., bromine (0.79 g, 4.9 mmol) was slowly added to a solution of 3',4'-dichloropropiophenone (1.0 g, 4.9 mmol) in diethyl ether (12 mL). The reaction mixture was warmed to rt and stirred for 2 h. The mixture was quenched with 10% $K_2CO_3$, extracted with EtOAc, washed with sodium thiosulfate, dried ($Na_2SO_4$), filtered, and concentrated. The crude residue was purified by chromatography on silica gel (hexanes/DCM, 1:1) to give the desired product as a white solid (1.3 g, 93%): Mp 52° C.; $^1$H NMR (400 MHz, CDCl$_3$) δ 8.10 (s, 1H), 7.84 (d, J=8.2 Hz, 2H), 7.57 (d, J=8.2 Hz, 2H), 5.17 (q, J=6.4 Hz, 1H), 1.90 (d, J=6.4 Hz, 3H); $^{13}$C NMR (100 MHz, DMSO-$d_6$, 100° C.) δ 191.3, 138.5, 133.8, 133.7, 131.1, 131.0, 128.0, 41.2, 20.0; IR (ATR, neat) 3351, 3079, 3001, 2934, 1683, 1582, 1377, 1219, 1150, 1031, 808 cm$^{-1}$; HRMS (ESI) m/z calcd for $C_9H_{18}OCl_2Br$ [M+H]$^+$ 280.9136, found 280.9145.

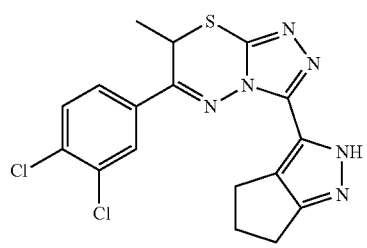 [SMILES: CC1Sc2nnc(-c3[nH]nc4c3CCC4)n2N=C1c1ccc(Cl)c(Cl)c1]

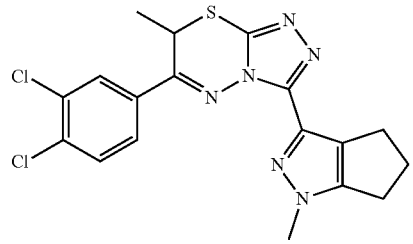

6-(3,4-Dichlorophenyl)-7-methyl-3-(2,4,5,6-tetrahydro-cyclopenta[c]pyrazol-3-yl)-7H-[1,2,4]triazolo[3,4-b][1,3,4]thiadiazine (UPCDC10263). A suspension of 22 (0.100 g, 0.450 mmol) and 23 (0.127 g, 0.450 mmol) in EtOH (4 mL) was heated to 95° C. under microwave irradiation for 60 min. The solvent was evaporated, and the crude residue was purified by chromatography on silica gel (10% MeOH/DCM) to afford the desired product UPCDC10263 (0.13 g, 71%) as a white powder: Mp 158° C.; $^{1}$H NMR (400 MHz, DMSO-$d_6$, 100° C.) δ 12.70 (br s, 1H), 8.24 (s, 1H), 7.98 (d, J=8.4 Hz, 1H), 7.82 (d, J=8.4 Hz, 1H), 4.97 (q, J=7.0 Hz, 1H), 2.72-2.66 (m, 4H), 2.43-2.32 (m, 2H), 1.48 (d, J=7.0 Hz, 3H); $^{13}$C NMR (100 MHz, DMSO-$d_6$, 100° C.) δ 155.9, 139.2, 134.3, 132.8, 131.8, 130.7, 128.8, 127.0, 31.3, 29.5, 23.4, 23.1, 18.5, 4 quaternary C were missing; IR (ATR, neat) 3279, 2921, 1508, 1454, 1303, 958 cm$^{-1}$; HRMS (ESI) m/z calcd for $C_{17}H_{15}N_6SCl_2$ 405.0456, found 405.0465.

Example 3

General Scheme for Alkylation and/or acylation of analogs 1, 2 and 3.

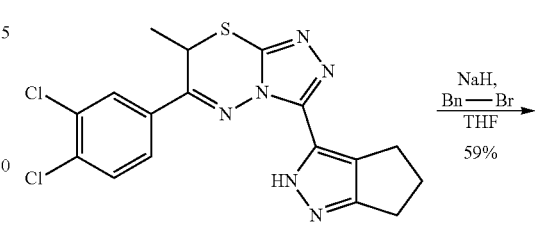

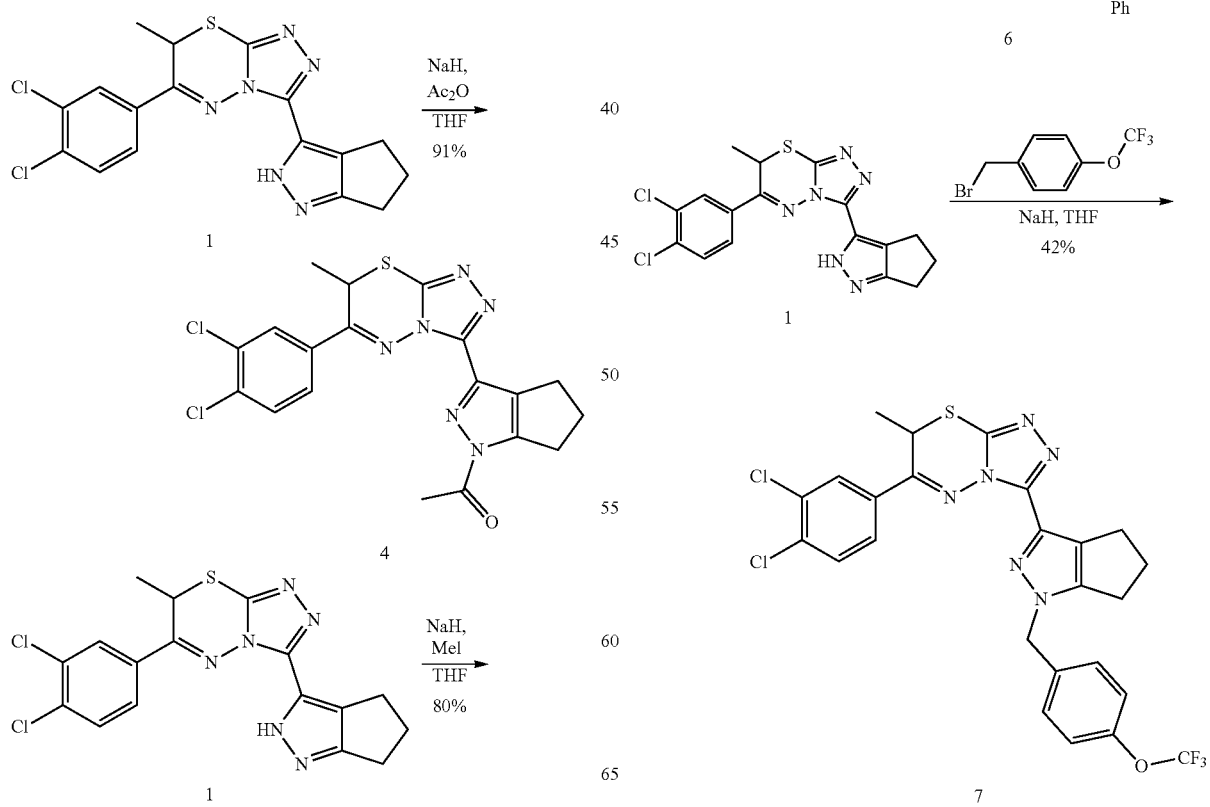

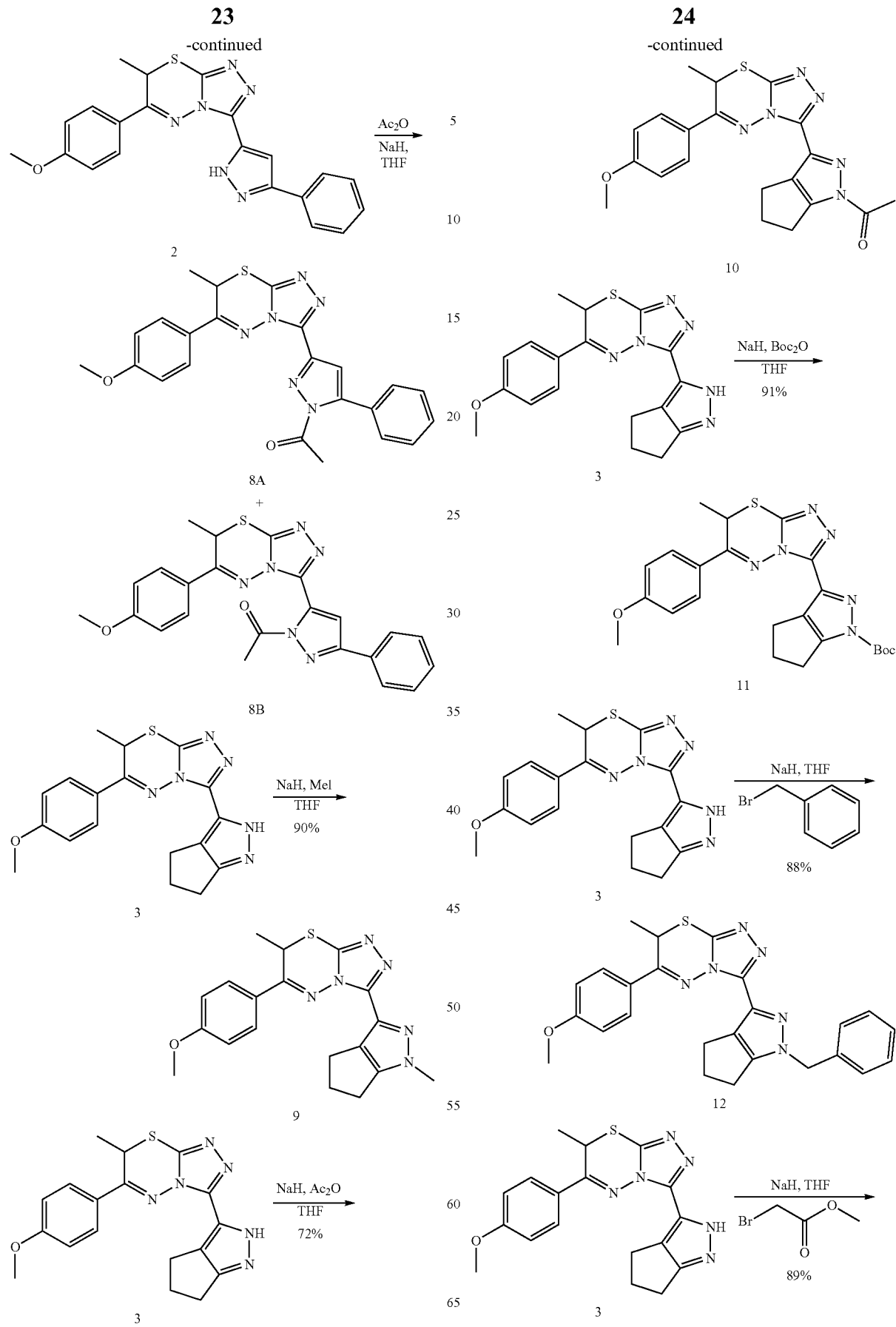

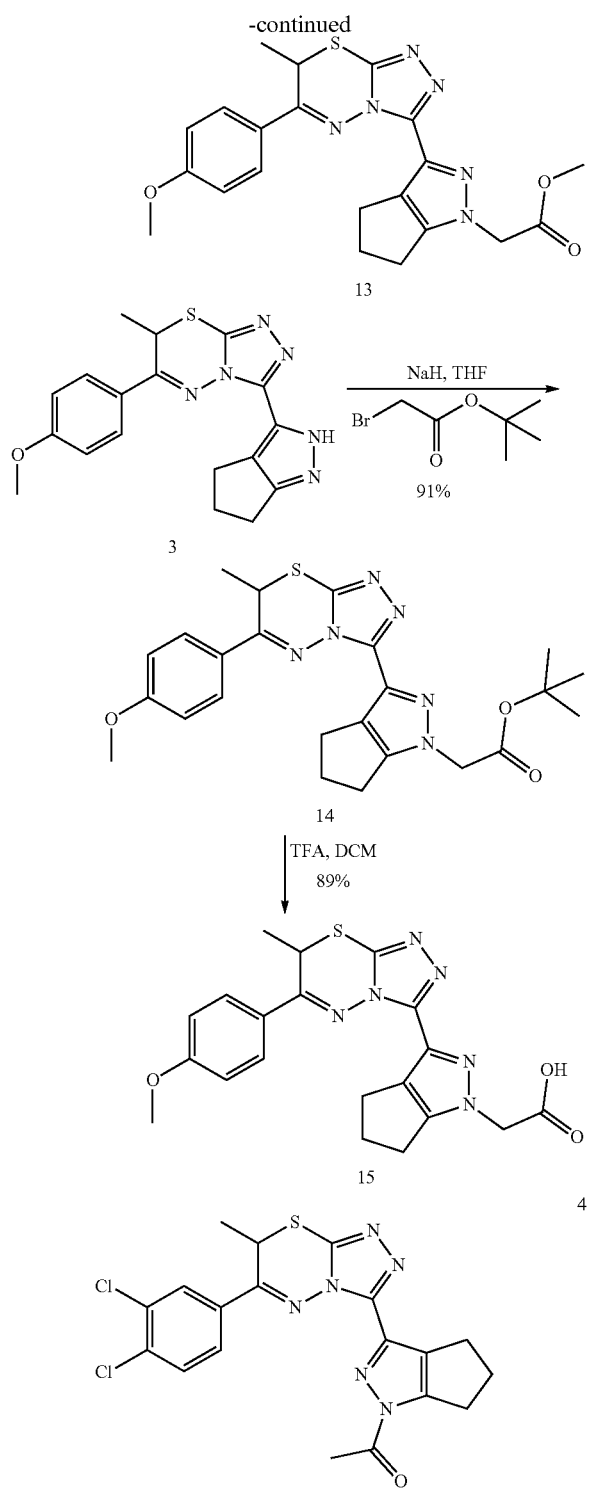

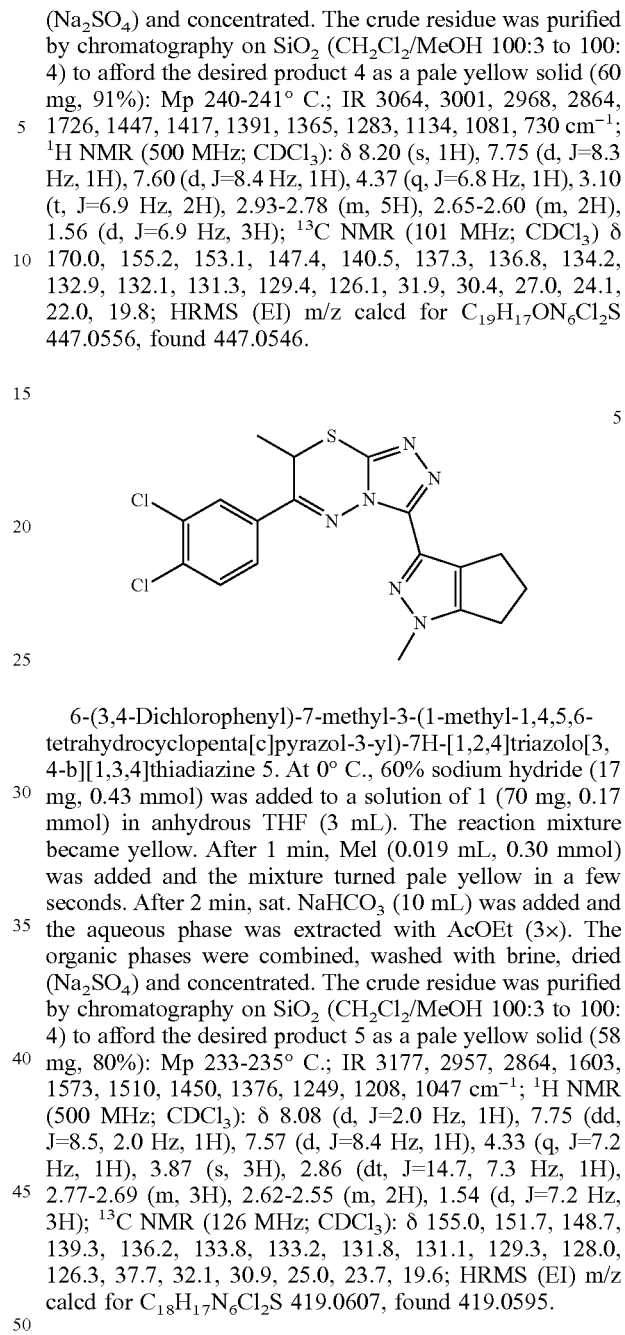

1-(3-(6-(3,4-Dichlorophenyl)-7-methyl-7H-[1,2,4]triazolo[3,4-b][1,3,4]thiadiazin-3-yl)-5,6-dihydrocyclopenta[c]pyrazol-1(4H)-yl)ethanone 4. At 0° C., 60% sodium hydride (15 mg, 0.37 mmol) was added to a solution of 1 (60 mg, 0.15 mmol) in anhydrous THF (3 mL). The reaction mixture became pale yellow. After 1 min, Ac$_2$O (0.028 mL, 0.30 mmol) was added and the mixture turned colorless in a few seconds. After 2 min, sat. NaHCO$_3$ (10 mL) was added and the aqueous phase was extracted with EtOAc (3×). The organic phases were combined, washed with brine, dried (Na$_2$SO$_4$) and concentrated. The crude residue was purified by chromatography on SiO$_2$ (CH$_2$Cl$_2$/MeOH 100:3 to 100:4) to afford the desired product 4 as a pale yellow solid (60 mg, 91%): Mp 240-241° C.; IR 3064, 3001, 2968, 2864, 1726, 1447, 1417, 1391, 1365, 1283, 1134, 1081, 730 cm$^{-1}$; $^1$H NMR (500 MHz; CDCl$_3$): δ 8.20 (s, 1H), 7.75 (d, J=8.3 Hz, 1H), 7.60 (d, J=8.4 Hz, 1H), 4.37 (q, J=6.8 Hz, 1H), 3.10 (t, J=6.9 Hz, 2H), 2.93-2.78 (m, 5H), 2.65-2.60 (m, 2H), 1.56 (d, J=6.9 Hz, 3H); $^{13}$C NMR (101 MHz; CDCl$_3$) δ 170.0, 155.2, 153.1, 147.4, 140.5, 137.3, 136.8, 134.2, 132.9, 132.1, 131.3, 129.4, 126.1, 31.9, 30.4, 27.0, 24.1, 22.0, 19.8; HRMS (EI) m/z calcd for C$_{19}$H$_{17}$ON$_6$Cl$_2$S 447.0556, found 447.0546.

6-(3,4-Dichlorophenyl)-7-methyl-3-(1-methyl-1,4,5,6-tetrahydrocyclopenta[c]pyrazol-3-yl)-7H-[1,2,4]triazolo[3,4-b][1,3,4]thiadiazine 5. At 0° C., 60% sodium hydride (17 mg, 0.43 mmol) was added to a solution of 1 (70 mg, 0.17 mmol) in anhydrous THF (3 mL). The reaction mixture became yellow. After 1 min, MeI (0.019 mL, 0.30 mmol) was added and the mixture turned pale yellow in a few seconds. After 2 min, sat. NaHCO$_3$ (10 mL) was added and the aqueous phase was extracted with AcOEt (3×). The organic phases were combined, washed with brine, dried (Na$_2$SO$_4$) and concentrated. The crude residue was purified by chromatography on SiO$_2$ (CH$_2$Cl$_2$/MeOH 100:3 to 100:4) to afford the desired product 5 as a pale yellow solid (58 mg, 80%): Mp 233-235° C.; IR 3177, 2957, 2864, 1603, 1573, 1510, 1450, 1376, 1249, 1208, 1047 cm$^{-1}$; $^1$H NMR (500 MHz; CDCl$_3$): δ 8.08 (d, J=2.0 Hz, 1H), 7.75 (dd, J=8.5, 2.0 Hz, 1H), 7.57 (d, J=8.4 Hz, 1H), 4.33 (q, J=7.2 Hz, 1H), 3.87 (s, 3H), 2.86 (dt, J=14.7, 7.3 Hz, 1H), 2.77-2.69 (m, 3H), 2.62-2.55 (m, 2H), 1.54 (d, J=7.2 Hz, 3H); $^{13}$C NMR (126 MHz; CDCl$_3$): δ 155.0, 151.7, 148.7, 139.3, 136.2, 133.8, 133.2, 131.8, 131.1, 129.3, 128.0, 126.3, 37.7, 32.1, 30.9, 25.0, 23.7, 19.6; HRMS (EI) m/z calcd for C$_{18}$H$_{17}$N$_6$Cl$_2$S 419.0607, found 419.0595.

3-(1-Benzyl-1,4,5,6-tetrahydrocyclopenta[c]pyrazol-3-yl)-6-(3,4-dichlorophenyl)-7-methyl-7H-[1,2,4]triazolo[3,4-b][1,3,4]thiadiazine 6. At 0° C., 60% sodium hydride (15 mg, 0.37 mmol) was added to a solution of 1 (60 mg, 0.15 mmol) in anhydrous THF (3 mL). The reaction mixture became yellow. After 1 min, BnBr (0.035 mL, 0.30 mmol) was added and the mixture turned pale yellow in a few seconds. After 15 min, sat. NaHCO$_3$ (10 mL) was added and the aqueous phase was extracted with AcOEt (3×). The organic phases were combined, washed with brine, dried (Na$_2$SO$_4$) and concentrated. The crude residue was purified by chromatography on SiO$_2$ (CH$_2$Cl$_2$/MeOH 100:3 to 100:4) to afford the desired product 6 as a pale yellow solid (43 mg, 59%): Mp 95-97° C.; IR 3065, 2931, 2863, 1581, 1547, 1450, 1376, 1301, 1137, 992, 727, 701 cm$^{-1}$; $^1$H NMR (400 MHz; CDCl$_3$): δ 8.07 (d, J=2.1 Hz, 1H), 7.73 (dd, J=8.5, 2.2 Hz, 1H), 7.54 (d, J=8.5 Hz, 1H), 7.36-7.29 (m, 5H), 5.31 (s, 2H), 4.31 (q, J=7.2 Hz, 1H), 2.89-2.82 (m, 1H), 2.76-2.69 (m, 1H), 2.57-2.48 (m, 4H), 1.55 (d, J=7.3 Hz, 3H); $^{13}$C NMR (101 MHz; CDCl$_3$): δ 154.9, 151.2, 148.7, 139.3, 136.24, 136.11, 133.8, 133.2, 132.1, 131.2, 129.3, 128.90, 128.74, 128.18, 128.02, 126.4, 55.4, 32.1, 30.9, 24.8, 24.1, 19.7; HRMS (EI) m/z calcd for C$_{24}$H$_{21}$N$_6$Cl$_2$S 495.0920, found 495.0920.

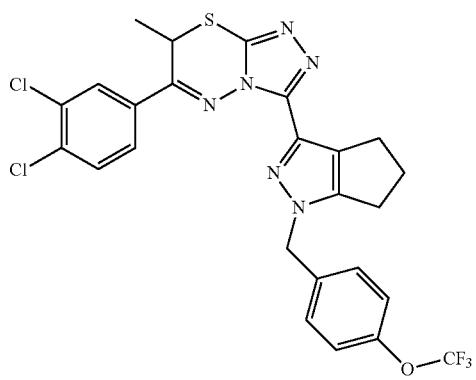

6-(3,4-Dichlorophenyl)-7-methyl-3-(1-(4-(trifluoromethoxy)benzyl)-1,4,5,6-tetrahydrocyclopenta[c]pyrazol-3-yl)-7H-[1,2,4]triazolo[3,4-b][1,3,4]thiadiazine 7. At −40° C., 60% sodium hydride (11 mg, 0.27 mmol) was added to a solution of rc-526-3 (55 mg, 0.14 mmol) in anhydrous THF (3 mL). The reaction mixture became yellow. After 1 min, 4-(Trifluoromethoxy)benzyl bromide (0.043 mL, 0.27 mmol) was added and the mixture was allowed to warm to 0° C. After 20 min at 0° C., sat. NaHCO$_3$ (10 mL) was added and the aqueous phase was extracted with AcOEt (3×). The organic phases were combined, washed with brine, dried (Na$_2$SO$_4$) and concentrated. The crude residue was purified by chromatography on SiO$_2$ (CH$_2$Cl$_2$/MeOH 100:2 to 100:3) to afford the desired product 7 as a pale yellow solid (33 mg, 42%): Mp 101-103° C.; IR 2964, 2931, 2863, 1510, 1450, 1252, 1215, 1159, 809, 679 cm$^{-1}$; $^1$H NMR (400 MHz; CDCl$_3$): δ 8.06 (d, J=2.1 Hz, 1H), 7.71 (dd, J=8.5, 2.2 Hz, 1H), 7.55 (d, J=8.5 Hz, 1H), 7.33 (d, J=8.7 Hz, 2H), 7.19 (d, J=8.0 Hz, 2H), 5.31 (s, 2H), 4.30 (q, J=7.3 Hz, 1H), 2.91-2.84 (m, 1H), 2.78-2.71 (m, 1H), 2.63-2.52 (m, 4H), 1.56 (d, J=7.3 Hz, 3H); $^{13}$C NMR (101 MHz; CDCl$_3$): δ 154.9, 151.3, 149.1, 148.6, 139.4, 136.4, 134.9, 133.9, 133.2, 132.5, 131.2, 129.36, 129.29, 128.9, 126.3, 121.4, 120.5 (q, $J_{F-C}$=257.4), 54.4, 32.1, 31.0, 24.9, 24.0, 19.7; HRMS (EI) m/z calcd for C$_{25}$H$_{20}$ON$_6$Cl$_2$F$_3$S 579.0743, found 579.0743.

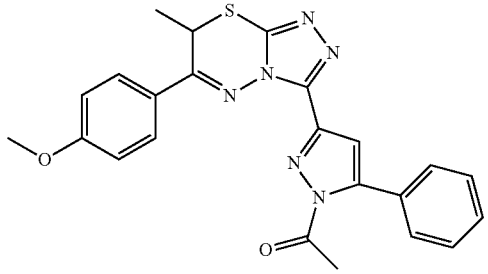

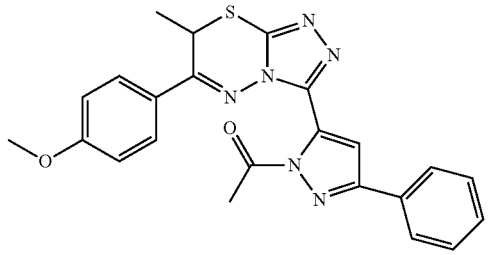

1-(3-(6-(4-Methoxyphenyl)-7-methyl-7H-[1,2,4]triazolo[3,4-b][1,3,4]thiadiazin-3-yl)-5-phenyl-1H-pyrazol-1-yl)ethanone 8 Å and 1-(5-(6-(4-methoxyphenyl)-7-methyl-7H-[1,2,4]triazolo[3,4-b][1,3,4]thiadiazin-3-yl)-3-phenyl-1H-pyrazol-1-yl)ethanone 8B. At 0° C., 60% sodium hydride (21 mg, 0.52 mmol) was added to a solution of 2 (85 mg, 0.15 mmol) in anhydrous THF (3 mL). The reaction mixture became pale yellow. After 1 min, Ac$_2$O (0.028 mL, 0.30 mmol) was added and the mixture turned colorless in a few seconds. After 2 min, sat. NaHCO$_3$ (10 mL) was added and the aqueous phase was extracted with AcOEt (3×). The organic phases were combined, washed with brine, dried (Na$_2$SO$_4$) and concentrated. The crude residue was purified by chromatography on SiO$_2$ (AcOEt/MeOH 100:1 to 100:3) to afford the product 8A (41 mg, 44%) and product 8B (42 mg, 45%)

8A:

Mp 114-115° C.; IR 3069, 2975, 2845, 1741, 1603, 1514, 1443, 1365, 1324, 1305, 1286, 1178, 1078, 1029, 981, 835, 730 cm$^{-1}$; $^1$H NMR (400 MHz; CDCl$_3$): δ 7.95-7.92 (m, 2H), 7.73 (d, J=9.0 Hz, 2H), 7.50-7.43 (m, 3H), 7.26 (s, 1H), 6.94 (d, J=9.0 Hz, 2H), 4.36 (q, J=7.3 Hz, 1H), 3.84 (s, 3H), 2.71 (s, 3H), 1.65 (d, J=7.3 Hz, 3H); $^{13}$C NMR (101 MHz; CDCl$_3$): δ 169.4, 162.8, 157.1, 154.1, 145.5, 140.7, 131.2, 130.9, 129.7, 129.05, 128.98, 126.4, 124.9, 114.6, 112.8, 55.6, 32.7, 22.8, 19.4; HRMS (EI) m/z calcd for C$_{23}$H$_{21}$O$_2$N$_6$S 445.1441, found 445.1429.

8B:

Mp 115-116° C.; IR 2964, 2927, 2856, 1745, 1607, 1514, 1447, 1420, 1365, 1301, 1257, 1178, 1029, 947, 835, 764, 727 cm$^{-1}$; $^1$H NMR (400 MHz; CDCl$_3$): δ 7.94-7.92 (m, 2H), 7.48-7.41 (m, 5H), 7.11 (s, 1H), 7.01 (d, J=8.9 Hz, 2H), 4.42 (q, J=7.3 Hz, 1H), 3.88 (s, 3H), 2.86 (s, 3H), 1.56 (d, J=7.2 Hz, 3H); $^{13}$C NMR (101 MHz; CDCl$_3$): δ 170.5, 163.0, 157.4, 146.9, 146.6, 141.7, 140.8, 130.5, 129.19, 129.15, 129.10, 128.1, 125.0, 114.8, 112.2, 55.7, 32.1, 23.9, 19.9; HRMS (EI) m/z calcd for C$_{23}$H$_{21}$O$_2$N$_6$S 445.1441, found 445.1435.

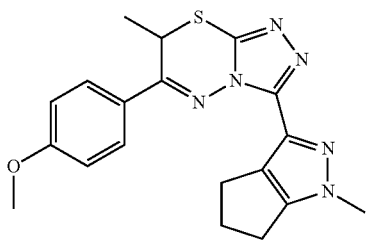

9

6-(4-Methoxyphenyl)-7-methyl-3-(1-methyl-1,4,5,6-tetrahydrocyclopenta[c]pyrazol-3-yl)-7H-[1,2,4]triazolo[3,4-b][1,3,4]thiadiazine 9. At 0° C., 60% sodium hydride (15 mg, 0.37 mmol) was added to a solution of 3 (55 mg, 0.15 mmol) in anhydrous THF (3 mL). The reaction mixture became pale yellow. After 1 min, MeI (0.019 mL, 0.30 mmol) was added and the mixture turned colorless in a few seconds. After 2 min, sat. NaHCO$_3$ (10 mL) was added and the aqueous phase was extracted several times with AcOEt. The organic phases were combined, washed with brine, dried (Na$_2$SO$_4$) and concentrated. The crude residue was purified by chromatography on SiO$_2$ (CH$_2$Cl$_2$/MeOH 100:4 to 100:6) to afford the desired product 9 as a pale yellow solid (51 mg, 89%): Mp 206-207° C.; IR 3070, 3007, 2945, 2919, 2856, 1603, 1551, 1512, 1450, 1419, 1390, 1303, 1258, 1180, 1068, 1012, 841 cm$^{-1}$; $^1$H NMR (400 MHz; CDCl$_3$) δ 7.88 (d, J=8.4 Hz, 2H), 6.99 (d, J=8.4 Hz, 2H), 4.32 (q, J=7.2 Hz, 1H), 3.88 (s, 6H), 2.88 (dt, J=14.8, 7.3 Hz, 1H), 2.81-2.70 (m, 3H), 2.60-2.52 (m, 2H), 1.54 (d, J=7.2 Hz, 3H); $^{13}$C NMR (101 MHz; CDCl$_3$) δ 162.7, 156.7, 151.5, 148.7, 139.4, 132.1, 129.1, 127.9, 125.6, 114.6, 55.7, 37.8, 32.4, 31.0, 25.3, 23.8, 19.8; HRMS (EI) m/z calcd for C$_{19}$H$_{21}$ON$_6$S 381.1492, found 381.1485.

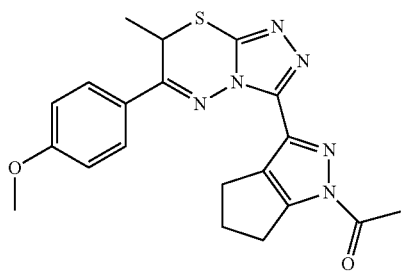

10

1-(3-(6-(4-Methoxyphenyl)-7-methyl-7H-[1,2,4]triazolo[3,4-b][1,3,4]thiadiazin-3-yl)-5,6-dihydrocyclopenta[c]pyrazol-1(4H)-yl)ethanone 10. At 0° C., 60% sodium hydride (15 mg, 0.37 mmol) was added to a solution of 3 (55 mg, 0.15 mmol) in anhydrous THF (3 mL). The reaction mixture became pale yellow. After 1 min, Ac$_2$O (0.028 mL, 0.30 mmol) was added and the mixture turned colorless in a few seconds. After 2 min, sat. NaHCO$_3$ (10 mL) was added and the aqueous phase was extracted several times with AcOEt. The organic phases were combined, washed with brine, dried (Na$_2$SO$_4$) and concentrated. The crude residue was purified by chromatography on SiO$_2$ (CH$_2$Cl$_2$/MeOH 100:4 to 100:6) and then recrystallized from AcOEt, to afford the desired product 10 as a white solid (44 mg, 72%): Mp 196-197° C.; IR 2923, 2852, 1726, 1603, 1555, 1443, 1305, 1257, 1175, 1029, 831 cm$^{-1}$; $^1$H NMR (400 MHz; CDCl$_3$) δ 7.92 (AB, J=9.0 Hz, 2H), 7.00 (AB, J=9.0 Hz, 2H), 4.39 (q, J=7.3 Hz, 1H), 3.89 (s, 3H), 3.12-3.05 (m, J=1.3 Hz, 2H), 2.87-2.75 (m, 5H), 2.64-2.56 (m, 2H), 1.56 (d, J=7.3 Hz, 3H). $^{13}$C NMR (101 MHz; CDCl$_3$) δ 170.1, 162.9, 157.1, 152.9, 147.4, 140.7, 137.5, 132.0, 129.1, 125.1, 114.7, 55.7, 32.1, 30.4, 27.0, 24.2, 21.9, 19.9; HRMS (EI) m/z calcd for C$_{20}$H$_{21}$O$_2$N$_6$S 409.1441, found 409.1428.

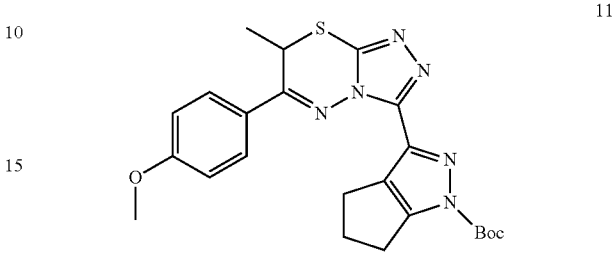

11 tert-Butyl 3-(6-(4-methoxyphenyl)-7-methyl-7H-[1,2,4]triazolo[3,4-b][1,3,4]thiadiazin-3-yl)-5,6-dihydrocyclopenta[c]pyrazole-1(4H)-carboxylate 11. At 0° C., 60% sodium hydride (15 mg, 0.37 mmol) was added to a solution of 3 (55 mg, 0.15 mmol) in anhydrous THF (3 mL). The reaction mixture became pale yellow. After 1 min, Boc$_2$O (66 mg, 0.30 mmol) was added and the mixture turned colorless in a few seconds. After 2 min, sat. NaHCO$_3$ (10 mL) was added and the aqueous phase was extracted several times with AcOEt. The organic phases were combined, washed with brine, dried (Na$_2$SO$_4$) and concentrated. The crude residue was purified by chromatography on SiO$_2$ (CH$_2$Cl$_2$/MeOH 100:4 to 100:6) to afford the desired product 11 as a pale yellow solid (64 mg, 91%): Mp 126-129° C.; IR 2976, 2939, 2864, 1760, 1742, 1604, 1514, 1440, 1417, 1320, 1294, 1152, 1089, 839 cm$^{-1}$; $^1$H NMR (400 MHz; CD$_2$Cl$_2$) δ 7.93 (AB, J=9.1 Hz, 2H), 7.00 (AB, J=9.1 Hz, 2H), 4.46 (q, J=7.3 Hz, 1H), 3.86 (s, 3H), 3.03-2.97 (m, J=1.4 Hz, 2H), 2.87-2.81 (m, 1H), 2.79-2.72 (m, 1H), 2.61-2.53 (m, 2H), 1.64 (s, 9H), 1.51 (d, J=7.3 Hz, 3H). $^{13}$C NMR (101 MHz; CD$_2$Cl$_2$) δ 163.1, 157.5, 153.8, 147.79, 147.62, 140.7, 137.7, 130.8, 129.4, 125.4, 114.8, 85.4, 55.9, 32.4, 30.3, 28.0, 27.64, 27.59, 24.6, 19.9. HRMS (EI) m/z calcd for C$_{23}$H$_{27}$O$_3$N$_6$S 467.1860, found 467.1853.

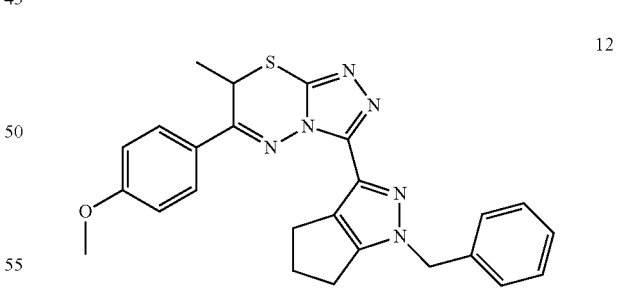

12

3-(1-Benzyl-1,4,5,6-tetrahydrocyclopenta[c]pyrazol-3-yl)-6-(4-methoxyphenyl)-7-methyl-7H-[1,2,4]triazolo[3,4-b][1,3,4]thiadiazine 12. At 0° C., 60% sodium hydride (16 mg, 0.40 mmol) was added to a solution of 3 (50 mg, 0.14 mmol) in anhydrous THF (3 mL). The reaction mixture became pale yellow. After 1 min, BnBr (0.030 mL, 0.27 mmol) was added and the mixture turned colorless in a few seconds. After 2 min, sat. NaHCO$_3$ (10 mL) was added and the aqueous phase was extracted several times with AcOEt. The organic phases were combined, washed with brine, dried (Na$_2$SO$_4$), and concentrated. The crude residue was purified by chromatography on SiO$_2$ (CH$_2$Cl$_2$/MeOH 100:4 to 100:6) and to afford the desired product 12 as a white solid (55 mg, 88%): Mp 104-105° C.; IR 3058, 2949, 2864, 1603, 1514, 1450, 1361, 1305, 1260, 1178, 1063, 1029, 839, 731, 701 cm$^{-1}$; $^1$H NMR (400 MHz; CDCl$_3$) δ 7.86 (AB, J=9.0 Hz, 2H), 7.37-7.28 (m, 5H), 6.96 (AB, J=9.0 Hz, 2H), 5.31 (s, 2H), 4.34 (t, J=7.2 Hz, 1H), 3.87 (s, 3H), 2.89-2.82 (m, 1H), 2.74-2.67 (m, 1H), 2.57-2.44 (m, 4H), 1.54 (d, J=7.2 Hz, 3H). $^{13}$C NMR (101 MHz; CDCl$_3$) δ 162.6, 156.7, 151.1, 148.6, 139.5, 136.2, 132.1, 129.1, 128.9, 128.6, 128.11, 128.07, 125.5, 114.6, 55.6, 55.3, 32.2, 30.9, 24.9, 24.1, 19.8. HRMS (EI) m/z calcd for C$_{25}$H$_{25}$ON$_6$S 457.1805, found 457.1802.

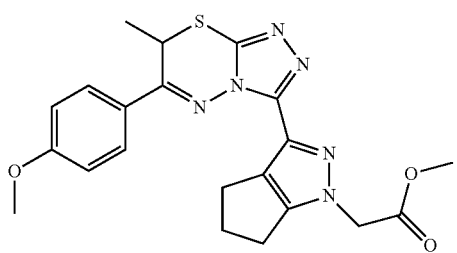

13

Methyl 2-(3-(6-(4-methoxyphenyl)-7-methyl-7H-[1,2,4]triazolo[3,4-b][1,3,4]thiadiazin-3-yl)-5,6-dihydrocyclopenta[c]pyrazol-1(4H)-yl)acetate 13 (RC-502-70). At 0° C., 60% sodium hydride (12 mg, 0.31 mmol) was added to a solution of 3 (45 mg, 0.12 mmol) in anhydrous THF (3 mL). The reaction mixture became pale yellow. After 1 min, methylbromoacetate (0.024 mL, 0.25 mmol) was added and the mixture turned colorless in a few seconds. After a 2 min, sat. NaHCO$_3$ (10 mL) was added and the aqueous phase was extracted several times with AcOEt. The organic phases were combined, washed with brine, dried (Na$_2$SO$_4$), and concentrated. The crude residue was purified by chromatography on SiO$_2$ (CH$_2$Cl$_2$/MeOH 100:4 to 100:6) to afford the desired product 13 as a semi-solid (48 mg, 89%): Mp 102-103° C.; IR 2954, 2920, 2864, 1749, 1607, 1514, 1447, 1309, 1257, 1227, 1178, 992, 839, 727 cm$^{-1}$; $^1$H NMR (500 MHz; CDCl$_3$) δ 7.87 (d, J=8.8 Hz, 2H), 6.99 (d, J=8.8 Hz, 2H), 4.91 (s, 2H), 4.34 (q, J=7.3 Hz, 1H), 3.87 (s, 3H), 3.77 (s, 3H), 2.90 (dt, J=14.7, 7.2 Hz, 1H), 2.80-2.69 (m, 3H), 2.60-2.54 (m, 2H), 1.53 (d, J=7.2 Hz, 3H); $^{13}$C NMR (126 MHz; CDCl$_3$) δ 168.0, 162.7, 156.8, 152.2, 148.3, 139.6, 133.2, 129.1, 128.7, 125.5, 114.6, 55.6, 52.7, 52.2, 32.3, 30.9, 25.3, 24.0, 19.8; HRMS (EI) m/z calcd for C$_{21}$H$_{23}$O$_3$N$_6$S 439.1547, found 439.1543.

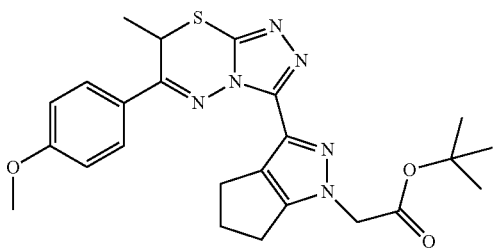

14 tert-Butyl 2-(3-(6-(4-methoxyphenyl)-7-methyl-7H-[1,2,4]triazolo[3,4-b][1,3,4]thiadiazin-3-yl)-5,6-dihydrocyclopenta[c]pyrazol-1(4H)-yl)acetate 14. At 0° C., 60% sodium hydride (18 mg, 0.44 mmol) was added to a solution of 3 (65 mg, 0.18 mmol) in anhydrous THF (3 mL). The reaction mixture became pale yellow. After 1 min, tert-butyl bromoacetate (0.053 mL, 0.35 mmol) was added and the mixture turned colorless in a few seconds. After 2 min, sat. NaHCO$_3$ (10 mL) was added and the aqueous phase was extracted several times with AcOEt. The organic phases were combined, washed with brine, dried (Na$_2$SO$_4$), and concentrated. The crude residue was purified by chromatography on SiO$_2$ (CH$_2$Cl$_2$/MeOH 100:4 to 100:6) to afford the desired product 14 as a white solid (76 mg, 89%): Mp 105-106° C.; IR 2968, 2939, 2864, 1741, 1607, 1514, 1447, 1305, 1256, 1238, 1152, 1029, 992, 839, 727 cm$^{-1}$; $^1$H NMR (400 MHz; CDCl$_3$) δ 7.86 (AB, J=9.0 Hz, 2H), 6.96 (AB, J=9.0 Hz, 2H), 4.79 (s, 2H), 4.33 (q, J=7.2 Hz, 1H), 3.86 (s, 3H), 2.91-2.84 (m, 1H), 2.79-2.66 (m, 3H), 2.60-2.51 (m, 2H), 1.52 (d, J=7.3 Hz, 3H), 1.46 (s, 9H). $^{13}$C NMR (101 MHz; CDCl$_3$) δ 166.6, 162.6, 156.6, 152.1, 148.4, 139.5, 132.8, 129.1, 128.4, 125.4, 114.5, 82.9, 55.6, 53.0, 32.2, 30.9, 28.1, 25.3, 23.9, 19.7; HRMS (EI) m/z calcd for C$_{24}$H$_{29}$O$_3$N$_6$S 481.2016, found 481.2001.

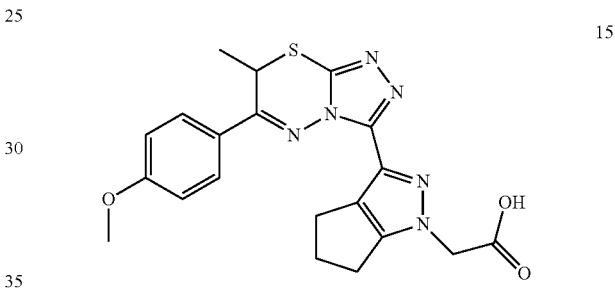

15

2-(3-(6-(4-Methoxyphenyl)-7-methyl-7H-[1,2,4]triazolo[3,4-b][1,3,4]thiadiazin-3-yl)-5,6-dihydrocyclopenta[c]pyrazol-1(4H)-yl)acetic acid 15. A solution of TFA and CH$_2$Cl$_2$ (1 mL and 0.5 mL respectively) was added to a solution of 14 (65 mg, 0.14 mmol) in CH$_2$Cl$_2$ (0.5 mL). The mixture was stirred for 3 h, then concentrated. Diethyl ether was added to the residue and the suspension was concentrated to afford a white solid. The crude residue was purified by chromatography on SiO$_2$ (eluent CH$_2$Cl$_2$/MEOH/AcOH 100:10:1) to afford the desired compound 15 as a white solid (51 mg, 89%): Mp 150-151° C.; IR 2931, 2849, 1730, 1607, 1581, 1514, 1447, 1342, 1305, 1272, 1174, 992, 958, 832 cm$^{-1}$; $^1$H NMR (400 MHz; CDCl$_3$) δ 8.50 (br s, 1H), 7.82 (d, J=8.4 Hz, 2H), 6.95 (d, J=8.4 Hz, 2H), 4.93 (s, 2H), 4.37 (q, J=6.3 Hz, 1H), 3.83 (s, 3H), 2.80-2.63 (m, 4H), 2.46 (br s, 2H), 1.47 (d, J=6.3 Hz, 3H); $^{13}$C NMR (101 MHz; CDCl$_3$) δ 169.9, 162.9, 157.8, 153.3, 147.9, 140.3, 131.5, 129.2, 128.0, 124.7, 114.7, 55.6, 52.3, 32.2, 30.6, 25.3, 23.7, 19.6; HRMS (EI) m/z calcd for C$_{20}$H$_{21}$O$_3$N$_6$S 425.1390, found 425.1389.

Example 4

Bioassay Evaluation

Compound samples (in 3-5 mg quantities) were evaluated in a variety of assays. All compound submissions were fully characterized (1H, 13C, IR, HRMS), satisfied purity criteria (≥95% LC/MC, ELS).

Compounds listed in Table 1 were synthesized using generally the conditions used in Examples 1 and 2. The Compounds are as follows:

TABLE 1
669 Series compounds with divergent Cal33 vs. STAT3 potency
| | | Growth Inhibition Cal33 (mean IC$_{50}$, µM) | STAT3 (mean IC$_{50}$, µM) |
|---|---|---|---|
| UPCDC87346005 | 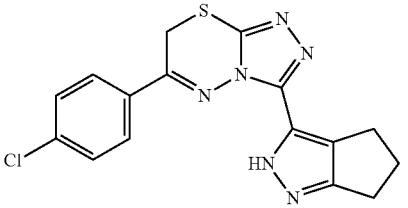 [SMILES: Clc1ccc(C2=Nn3c(nnc3-c3[nH]nc4c3CCC4)SC2)cc1] | 0.77 | 40.00 |
| UPCDC10073 | 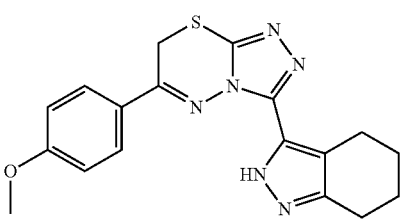 [SMILES: COc1ccc(C2=Nn3c(nnc3-c3[nH]nc4c3CCCC4)SC2)cc1] | 0.20 | 17.01 |
| UPCDC10084 | 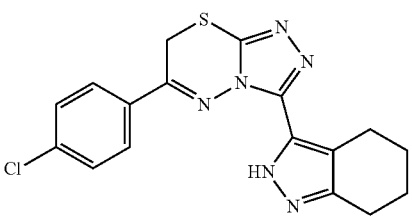 [SMILES: Clc1ccc(C2=Nn3c(nnc3-c3[nH]nc4c3CCCC4)SC2)cc1] | 0.60 | 21.34 |
| UPCDC10089 | 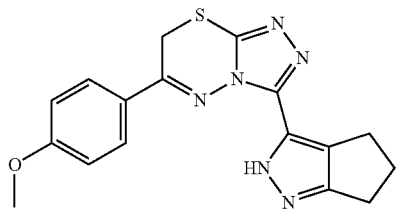 [SMILES: COc1ccc(C2=Nn3c(nnc3-c3[nH]nc4c3CCC4)SC2)cc1] | 0.15 | 35.92 |
| UPCDC10115 | 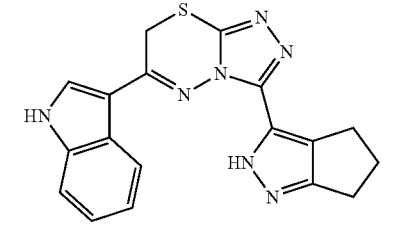 [SMILES: c1ccc2c(C3=Nn4c(nnc4-c4[nH]nc5c4CCC5)SC3)c[nH]c2c1] | 0.21 | 38.00 |
| UPCDC10262 | 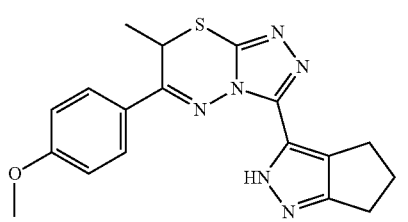 [SMILES: COc1ccc(C2=Nn3c(nnc3-c3[nH]nc4c3CCC4)SC2C)cc1] | 0.18 | 8.78 |

TABLE 1-continued

669 Series compounds with divergent Cal33 vs. STAT3 potency

| Compound | Growth Inhibition Cal33 (mean IC$_{50}$, µM) | STAT3 (mean IC$_{50}$, µM) |
|---|---|---|
| UPCDC10281 | 0.44 | 7.21 |
| UPCDC10305 | 0.47 | 5.14 |
| UPCDC10318 | 0.40 | 8.47 |
| UPCDC10332 | 0.16 | 14.33 |
| UPCDC10352 | 0.21 | 27.56 |

Additional compounds were then synthesized that showed greater structure activity relationships ("SAR") with respect to potency, selectivity, solubility, and permeability criteria.

For Example, FIG. 1 shows representative improvements.

Figure 3:
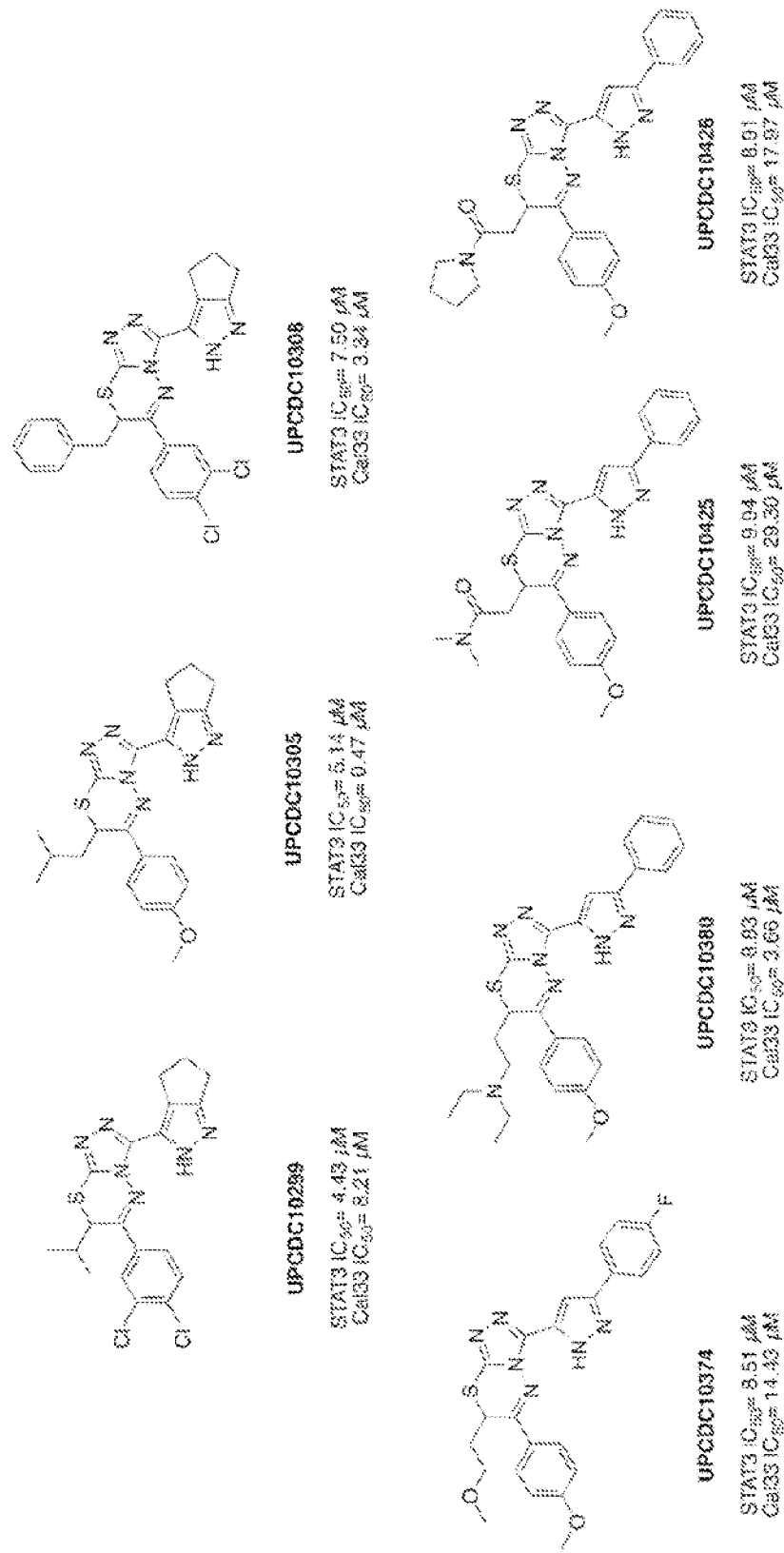
FIG. 3 shows an embodiment of representative alkyl and polar α-substitutions.

Further modifications were made, and the SAR was explored. For example, for R$_1$ in FIG. 1 the cyclopentylpyrazole-containing series and the phenylpyrazole containing series. Within these two sub-series, the targeted modifications at the R$_3$-position of the scaffold improved solubility and potency. Further modifications to the phenylpyrazole group with the synthesis of new cycloalkyl- and cycloheteroalkyl-fused pyrazoles. Analogs were synthesized and SAR analysis of the developments is summarized in FIG. 2. The mono-substitution at $R_3$ not only improved the metabolic stability, but it also increased the potency of the compound. During this phase, the incorporation of polar groups (amide, esters, ethers, amines) at the $R_3$-position was targeted to improve the solubility of the target compounds. Bulky alkyl substitutions (UPCDC10299, 10305, 10308) and select polar functional groups (UPCDC10384, 10380, 10425, 10426) were well-tolerated and maintained STAT3 potency ($IC_{50}$<10 µM) (FIG. 3). Various $R_2$-substitutions including diverse aryl substitutions are preferred but specifically, p-methoxyphenyl and p-chlorophenyl substituents promoted growth inhibition activity in Cal33 cells.

Figure 4:
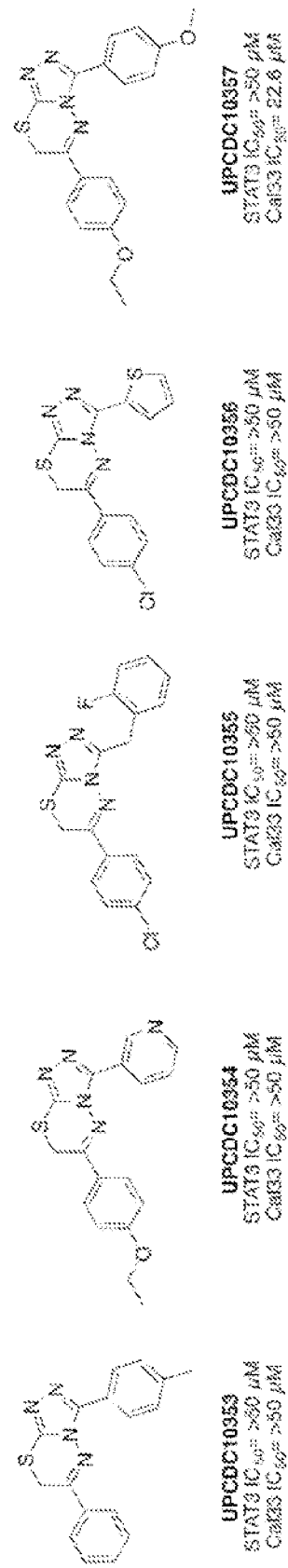
FIG. 4 shows an embodiment of representative pyrazole replacements.

Pyrazole replacements at $R_1$ with related N-heterocycles (triazoles, imidazoles), alkyl groups, and various aryl groups (phenyl, benzyl, thiophenyl, pyridyl) had poor-to-no activity in both HCS STAT3 and Cal33 growth inhibition assays compared to UPCDC864669 (FIG. 4).

Figure 6:
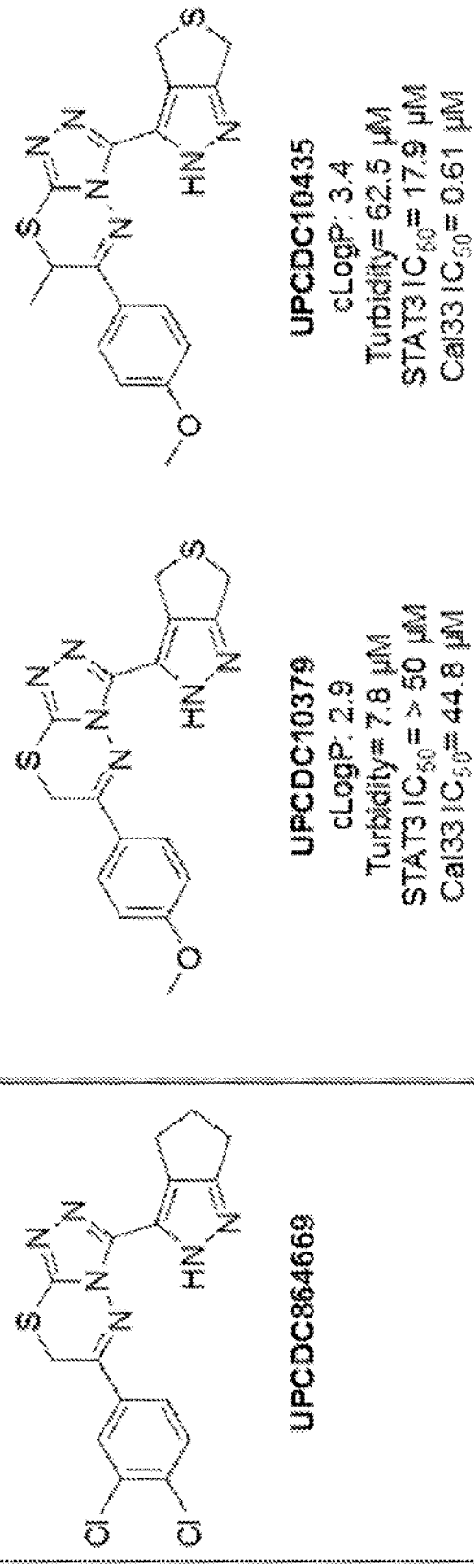
FIG. 6 shows an embodiment of fused heterocyclic pyrazoles.

Having established the necessity of the pyrazole at the $R_1$-position, substituted pyrazoles were explored (FIG. 5) as well as fused heterocyclic pyrazoles. Heterocyclic pyrazoles significantly improved the c Log P values, as the resultant compounds were predicted to be more soluble than UPCDC864669. Unfortunately, these compounds were less-to-inactive compared to the lead compound 669 (FIG. 6).

VII. Additional Species

The following table lists compounds of the present disclosure that were synthesized and the associated IC50 values (Cal33 and STAT3) were measured. To be sure, the compounds in the following table utilize dashed/solid and squiggled lines to represent bonding points. For a fused substitution, such as 10476, the moiety

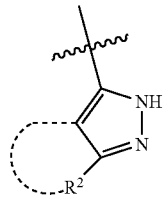

has substitution of

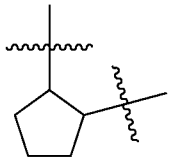 [SMILES: *C1CCCC1*]

at $R^2$. Thus, the moiety would be:

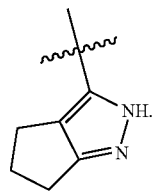 [SMILES: *c1[nH]nc2c1CCC2]

On the other hand, for non-fused compounds, such as 10475 the moiety

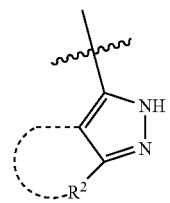

has substitution of

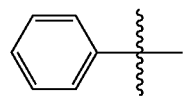 [SMILES: *c1ccccc1]

$R^2$. Thus, the moiety would be:

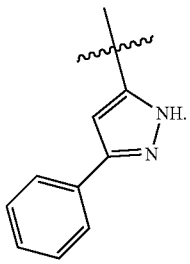 [SMILES: *c1cc(-c2ccccc2)n[nH]1]

TABLE 2

| UP-CDC # | R | R₁ | | R₂ | Cal33 (IC50) | STAT3 (IC50) |
|---|---|---|---|---|---|---|
| 10135 | Me | phenyl | pyrazole-NH (R²) | 4-F-phenyl | 33.4 | 3.8 |
| 10173 | Me | phenyl | pyrazole-NH (R²) | cyclopentyl | 41.77 | 18.2 |
| 10174 | Me | phenyl | pyrazole-NH (R²) | 4-Cl-phenyl | 35.5 | 5.7 |

TABLE 2-continued
| UP-CDC # | R | R₁ | | R₂ | Cal33 (IC50) | STAT3 (IC50) |
|---|---|---|---|---|---|---|
| 10175 | Me | 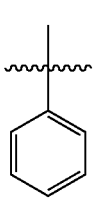 | 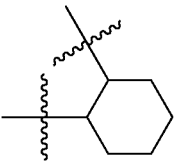 | 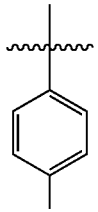 | 40.2 | 22.4 |
| 10204 | Me | 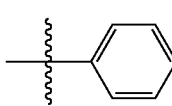 | | 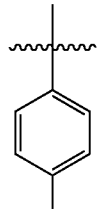 | 33.0 | 4.2 |
| 10205 | Me | 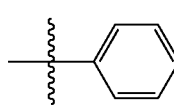 | | | 2.1, 2.0 | 3.8, 12.8 |

TABLE 2-continued

| UP-CDC # | R | R₁ | | R₂ | Cal33 (IC50) | STAT3 (IC50) |
|---|---|---|---|---|---|---|
| 10131 10260 10261 | Me | phenyl | pyrazole (NH, N, R²) | phenyl | 26.3, 42.7, 40.0 | 3.0, 4.8, 12.3 |
| 10262 | Me | 4-MeO-phenyl | pyrazole (NH, N, R²) | cyclopentyl (1,2-disubstituted) | 0.18 | 8.8 |
| 10263 | Me | 3,4-dichlorophenyl | pyrazole (NH, N, R²) | cyclopentyl (1,2-disubstituted) | 1.3, 3.0 | 8.5, 11.0 |

TABLE 2-continued
| UP-CDC # | R | R₁ | | R₂ | Cal33 (IC50) | STAT3 (IC50) |
|---|---|---|---|---|---|---|
| 10264 | Me, Me | 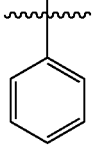 | 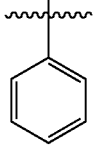 | 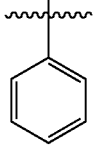 | 50 | 45.6 |
| 10268 | Me, Me | 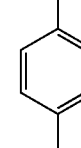 | 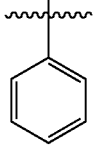 | 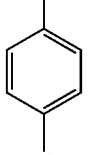 | 50 | 38.2 |
| 10281 | Me | 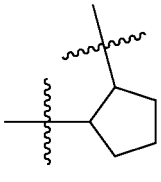 | 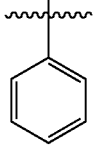 | 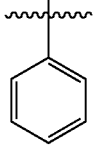 | 0.44 | 7.21 |

TABLE 2-continued
| UP-CDC # | R | R$_1$ | | R$_2$ | Cal33 (IC50) | STAT3 (IC50) |
|---|---|---|---|---|---|---|
| 10282 | Me | 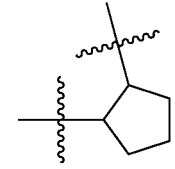 | 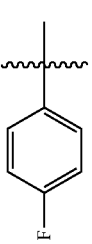 | 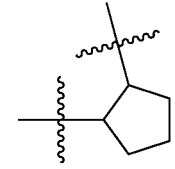 | 31.3 | 27.7 |
| 10283 | Me, Me | 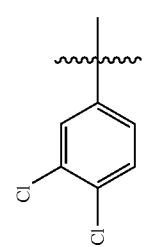 | 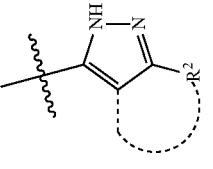 | 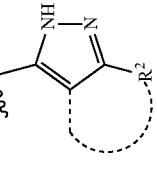 | 50 | 18.6 |
| 10298 | Ph | 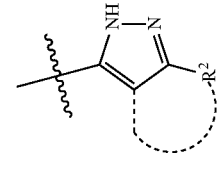 | 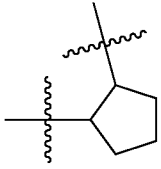 | 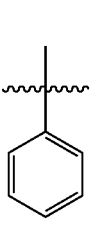 | 1.1 | 26.5 |

TABLE 2-continued

| UP-CDC # | R | R₁ | | R₂ | Cal33 (IC50) | STAT3 (IC50) |
|---|---|---|---|---|---|---|
| 10299 | isobutyl | 3,4-dichlorophenyl | pyrazole (NH, N, R²) | cyclopentyl | 8.2 | 4.4 |
| 10304 | isopentyl | 3,4-dichlorophenyl | pyrazole (NH, N, R²) | cyclopentyl | 3.5 | 27.1 |
| 10305 | isopentyl | 4-methoxyphenyl | pyrazole (NH, N, R²) | cyclopentyl | 0.47 | 5.1 |

TABLE 2-continued

| UP-CDC # | R | R₁ | | R₂ | Cal33 (IC50) | STAT3 (IC50) |
|---|---|---|---|---|---|---|
| 10307 | isobutyl | 4-MeO-phenyl | NH-pyrazole-R² (fused) | phenyl | 11.5 | 13.6 |
| 10308 | benzyl | 3,4-diCl-phenyl | NH-pyrazole-R² (fused) | cyclopentyl (1,2-disub) | 3.3 | 7.5 |
| 10309 | benzyl | 3,4-diCl-phenyl | NH-pyrazole-R² (fused) | phenyl | ND | 22.6 |

TABLE 2-continued

| UP-CDC # | R | R₁ | | R₂ | Cal33 (IC50) | STAT3 (IC50) |
|---|---|---|---|---|---|---|
| 10318 | isopropyl | 4-MeO-phenyl | pyrazole-R² (fused) | cyclopentane-1,2-diyl | 0.40 | 8.5 |
| 10319 | isopropyl | 4-MeO-phenyl | pyrazole-R² (fused) | phenyl | 20.0 | 21.6 |
| 10320 | benzyl | 4-MeO-phenyl | pyrazole-R² (fused) | cyclopentane-1,2-diyl | 0.83 | 19.5 |

TABLE 2-continued

| UP-CDC # | R | R₁ | | R₂ | Cal33 (IC50) | STAT3 (IC50) |
|---|---|---|---|---|---|---|
| 10321 | benzyl | 4-MeO-phenyl | pyrazole (NH, R²) | phenyl | ND | 5.8 |
| 10352 | Me | 4-MeO-phenyl | phenyl | — | 0.21 | 27.6 |
| 10371 | 2-aminoethyl | 4-MeO-phenyl | pyrazole (NH, R²) | — | 24.1 | 11.7 |
| 10373 | 2-methoxyethyl | 4-MeO-phenyl | pyrazole (NH, R²) | 4-Cl-phenyl | 4.8 | 33.2 |

TABLE 2-continued
| UP-CDC # | R | R₁ | | R₂ | Cal33 (IC50) | STAT3 (IC50) |
|---|---|---|---|---|---|---|
| 10374 |  | 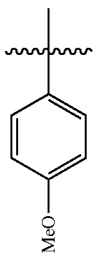 MeO | 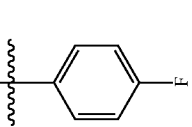 | 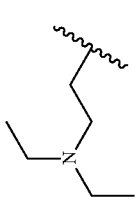 F | 14.4 | 8.5 |
| 10380 | 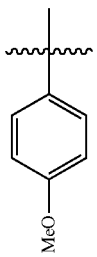 | 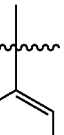 MeO | 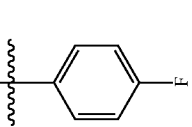 | 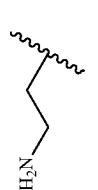 | 3.7 | 8.8 |
| 10383 | 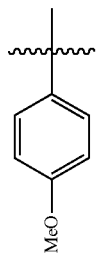 H₂N | 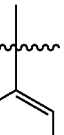 MeO | 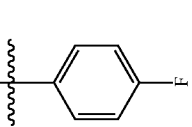 | 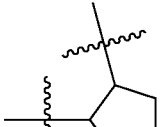 | 2.5 | 31.2 |

TABLE 2-continued
| UP-CDC # | R | R₁ | R₂ | Cal33 (IC50) | STAT3 (IC50) |
|---|---|---|---|---|---|
| 10384 | Et | | | 0.22 | 24.0 |
| 10403 | 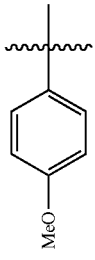 | 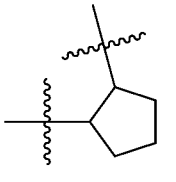 | 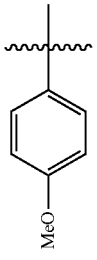 | 0.93 | 49.2 |
| 10410 | 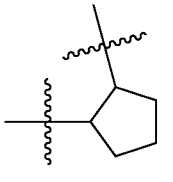 | 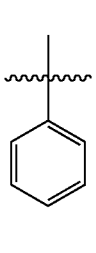 | 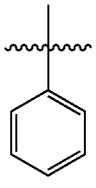 | 43.5 | 37.3 |

TABLE 2-continued
| UP-CDC # | R | R₁ | R₂ | Cal33 (IC50) | STAT3 (IC50) |
|---|---|---|---|---|---|
| 10411 | 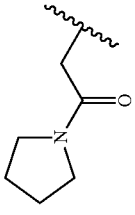 | 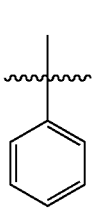 phenyl | 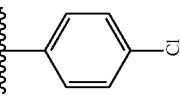 pyrazole-R² | 21.6 | 11.1 |
| 10420 | Me | 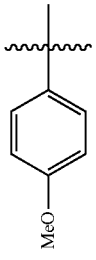 4-MeO-phenyl | 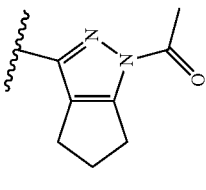 N-methyl cyclopenta-pyrazole | 0.38 | 46.1 |
| 10421 | Me | 4-MeO-phenyl | N-acetyl cyclopenta-pyrazole | 0.26 | 37.1 |

TABLE 2-continued
| UP-CDC # | R | R₁ | R₂ | Cal33 (IC50) | STAT3 (IC50) |
|---|---|---|---|---|---|
| 10422 | Me | 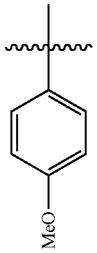 | 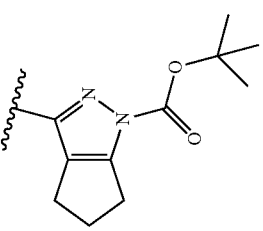 | 0.38 | 34.7 |
| 10423 | 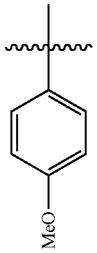 | 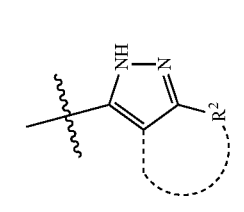 | 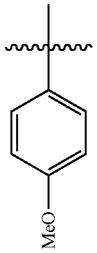 | 37.9 | 17.9 |
| 10425 | 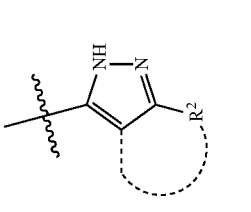 | (MeO-phenyl) | (phenyl) | 29.3 | 9.9 |

TABLE 2-continued
| UP-CDC # | R | R₁ | | R₂ | Cal33 (IC50) | STAT3 (IC50) |
|---|---|---|---|---|---|---|
| 10426 | 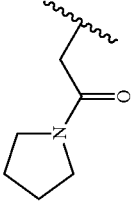 | 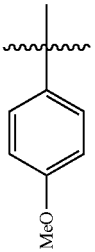 | 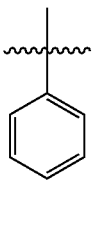 | 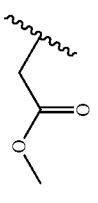 | 20.5 | 9.1 |
| 10427 | 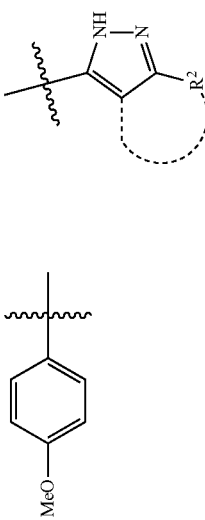 | 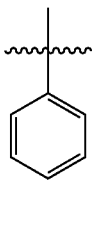 | 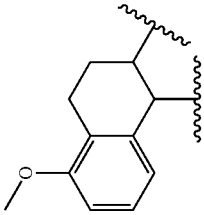 | 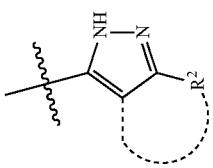 | 34.5 | 11.6 |
| 10434 | 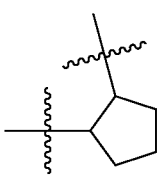 | | | | 47.4 | 32.0 |

TABLE 2-continued
| UP-CDC # | R | R₁ | R₂ | Cal33 (IC50) | STAT3 (IC50) |
|---|---|---|---|---|---|
| 10435 | Me | 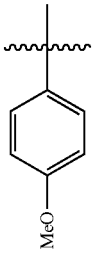 | 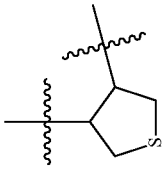 | 0.63 | 33.9 |
| 10437 | Me | 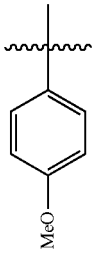 | 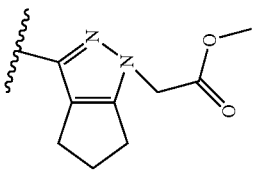 | 2.8 | 25.3 |
| 10438 | Me | 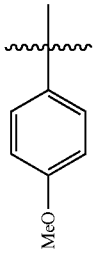 | 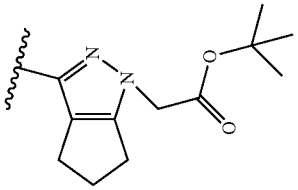 | 49.6 | 34.1 |

TABLE 2-continued

| UP-CDC # | R | R₁ | R₂ | Cal33 (IC50) | STAT3 (IC50) |
|---|---|---|---|---|---|
| 10439 | Me | 4-MeO-C₆H₄ | 3-(1-benzyl-5,6-dihydro-4H-cyclopenta[c]pyrazol-3-yl) | 1.7 | 7.6 |
| 10448 | ethoxycarbonylmethyl | 4-MeO-C₆H₄ | 1H-pyrazol-3-yl | 13.6 | 15.5 |
| 10458 | Me | 3,4-diCl-C₆H₃ | 1-acetyl-5,6-dihydro-4H-cyclopenta[c]pyrazol-3-yl | 4.5 | 22.7 |
| 10469 | Me | 3,4-diCl-C₆H₃ | 1-methyl-5,6-dihydro-4H-cyclopenta[c]pyrazol-3-yl | 3.1 | 7.8 |

TABLE 2-continued

| UP-CDC # | R | R₁ | | R₂ | Cal33 (IC50) | STAT3 (IC50) |
|---|---|---|---|---|---|---|
| 10470 | Me | 4-(F₃C)-phenyl | 3-R²-1H-pyrazol-5-yl | 1,2-disubstituted cyclopentyl | 1.4 | 24.4 |
| 10471 | Me | 3-(MeO)-phenyl | 3-R²-1H-pyrazol-5-yl | 1,2-disubstituted cyclopentyl | 3.9 | 40.1 |
| 10472 | Me | 4-Me-phenyl | 3-R²-1H-pyrazol-5-yl | 1,2-disubstituted cyclopentyl | 0.18 | 41.1 |

TABLE 2-continued

| UP-CDC # | R | R₁ | | R₂ | Cal33 (IC50) | STAT3 (IC50) |
|---|---|---|---|---|---|---|
| 10473 | Me | 4-Me-C₆H₄ | 3-R²-1H-pyrazol-5-yl | phenyl | 12.0 | 14.1 |
| 10474 | Me | 4-F₃CO-C₆H₄ | 3-R²-1H-pyrazol-5-yl | phenyl | 50 | 24.2 |
| 10475 | Me | 3-MeO-C₆H₄ | 3-R²-1H-pyrazol-5-yl | phenyl | 12.4 | 7.1 |

TABLE 2-continued

| UP-CDC # | R | R₁ | R₂ | Cal33 (IC50) | STAT3 (IC50) |
|---|---|---|---|---|---|
| 10476 | Me | 4-Br-phenyl | | 0.79 | 18.6 |
| 10477 | Me | 3,4-diCl-phenyl | 1H-pyrazole with fused cyclopentane, N-(4-CF₃O-benzyl) | 34.3 | 31.0 |
| 10478 | Me | 4-CF₃-phenyl | cyclopentane-1,2-diyl | 50 | 35.9 |
| 10479 | Me | 4-MeO-phenyl | 1-acetyl-5-phenyl-1H-pyrazol-3-yl | 38.1 | 7.9 |

TABLE 2-continued
| UP-CDC # | R | R₁ | R₂ | Cal33 (IC50) | STAT3 (IC50) |
|---|---|---|---|---|---|
| 10480 | Me | 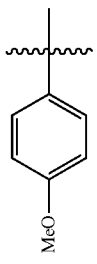 4-MeO-phenyl | 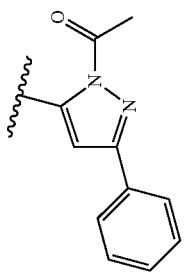 N-acetyl-3-phenyl-pyrazole | 30.4 | 6.3 |
| 10491 | Me | 3,4-dichlorophenyl | 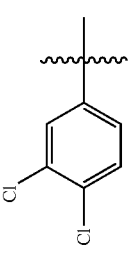 1-benzyl-cyclopenta-pyrazole | 17.4 | 5.9 |
| 10493 | Me | 4-MeO-phenyl | 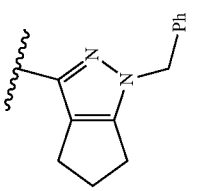 1H-pyrazole with R² | 13.7 | 26.2 |
| 10494 | Me | 3,4-diMeO-phenyl | 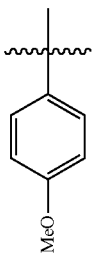 1H-pyrazole with R² | 5.7 | 25.1 |
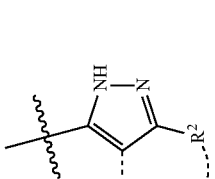
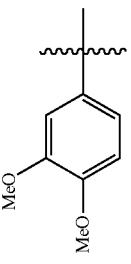
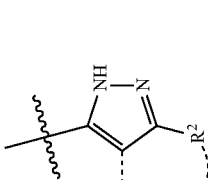

TABLE 2-continued

| UP-CDC # | R | R₁ | | R₂ | Cal33 (IC50) | STAT3 (IC50) |
|---|---|---|---|---|---|---|
| 10495 | Me | 3,4-diMeO-phenyl | pyrazole-R² | phenyl | 13.1 | 7.6 |
| 10510 | Me | 3,4-diF-phenyl | pyrazole-R² | cyclopentyl(di-subst) | 50 | 47.1 |
| 10511 | Me | 4-MeO-phenyl | pyrazole-R² | phenyl | 28.0 | 7.6 |

TABLE 2-continued
| UP-CDC # | R | R₁ | R₂ | Cal33 (IC50) | STAT3 (IC50) |
|---|---|---|---|---|---|
| 10512 | Me |  4-MeO-phenyl | 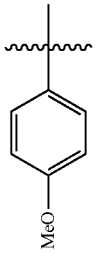 N-benzyl pyrrolidine | 4.6 | 27.0 |
| 10521 | Me | 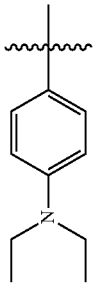 4-(NEt₂)-phenyl | 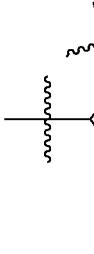 cyclopentane | 1.0 | 6.6 |
| 10522 | Me | 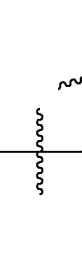 4-morpholinyl-phenyl | 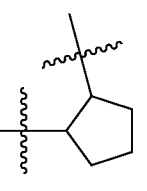 phenyl | 9.6 | 39.3 |

TABLE 2-continued
| UP-CDC # | R | R₁ | R₂ | Cal33 (IC50) | STAT3 (IC50) |
|---|---|---|---|---|---|
| 10532 | Me | 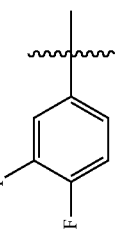 |  | 14.2 | 8.6 |
| 10534 | Me | | | 50 | 26.2 |
| 10535 | Me | 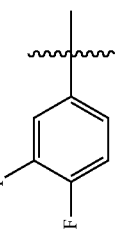 | 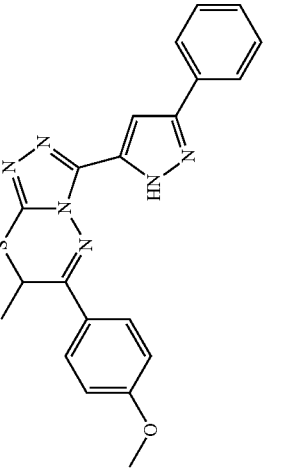 | 6.3 | 7.0 |

TABLE 2-continued

| UP-CDC # | R | R₁ | R₂ | Cal33 (IC50) | STAT3 (IC50) |
|---|---|---|---|---|---|
| 10536 | Me | 3-methoxyphenyl | 3-chlorophenyl | 9.3 | 9.1 |
| 10537 | Me | 3,4-dichlorophenyl | 4-chlorophenyl | 7.6 | 16.0 |
| 10538 | Me | 3,4-dichlorophenyl | 3-chlorophenyl | 13.7 | 32.2 |

TABLE 2-continued
| UP-CDC # | R | R₁ | R₂ | Cal33 (IC50) | STAT3 (IC50) |
|---|---|---|---|---|---|
| 10539 | Me | 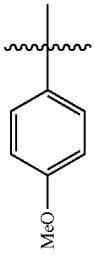 4-MeO-C₆H₄ | 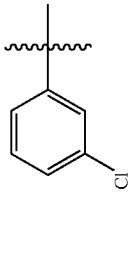 3-Cl-C₆H₄ | 12.7 | 8.7 |
| 10540 | Me | 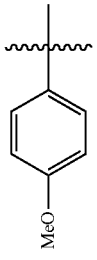 4-MeO-C₆H₄ | 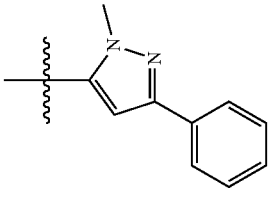 1-methyl-3-phenyl-1H-pyrazol-5-yl | 1.3 | 4.7 |
| 10542 | Me | 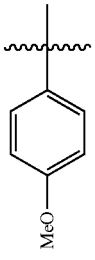 4-MeO-C₆H₄ | 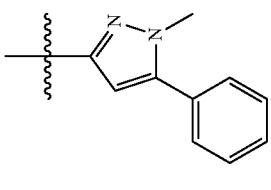 1-methyl-5-phenyl-1H-pyrazol-3-yl | 15.1 | 6.5 |

TABLE 2-continued
| UP-CDC # | R | R₁ | R₂ | Cal33 (IC50) | STAT3 (IC50) |
|---|---|---|---|---|---|
| 10543 | Me | 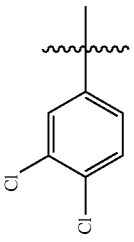 | 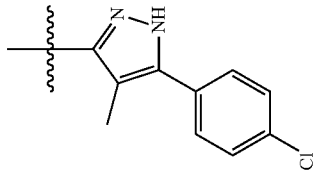 | 35.0 | 4.8 |
| 10547 | Me | 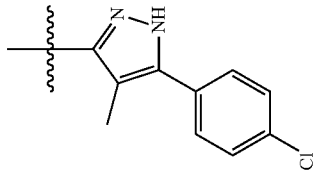 | 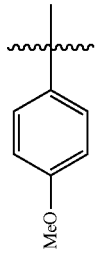 | 1.3 | 7.3 |

TABLE 2-continued

| UP-CDC # | R | R₁ | R₂ | Cal33 (IC50) | STAT3 (IC50) |
|---|---|---|---|---|---|
| 10554 | isopropyl | 4-MeO-phenyl | 1-methyl-5-phenyl-pyrazol-3-yl | 19.1 | 8.3 |
| 10555 | Me | 4-(diethylamino)phenyl | 1-methyl-5-phenyl-pyrazol-3-yl | 10.5 | 3.7 |
| 10556 | isopropyl | 3,4-dichlorophenyl | 1-methyl-5-phenyl-pyrazol-3-yl | 48.6 | 27.3 |

TABLE 2-continued
| UP-CDC # | R | R₁ | R₂ | Cal33 (IC50) | STAT3 (IC50) |
|---|---|---|---|---|---|
| 10559 | Me | 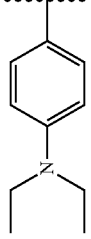 | 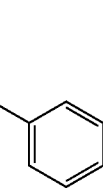 | 27.5 | 5.7 |
| 10562 | 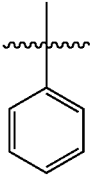 [SMILES: *c1ccccc1] | 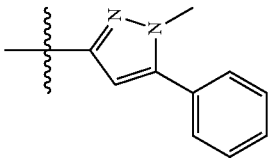 | 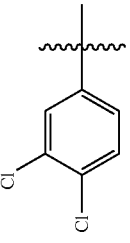 | 50 | 12.2 |
| 10579 | Me | 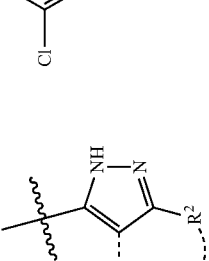 | | 2.7 | Peak1 7.1 |

TABLE 2-continued
| UP-CDC # | R | R₁ | R₂ | Cal33 (IC50) | STAT3 (IC50) |
|---|---|---|---|---|---|
| 10580 | Me |  | 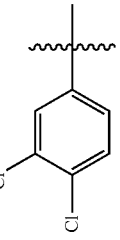 | 21.8 | Peak2 13.8 |

Example 5
Biological Activity

Compounds 1a and 2b (below) were measured for Biological Activity and Physicochemical Properties. The results are summarized in the following table

TABLE 3

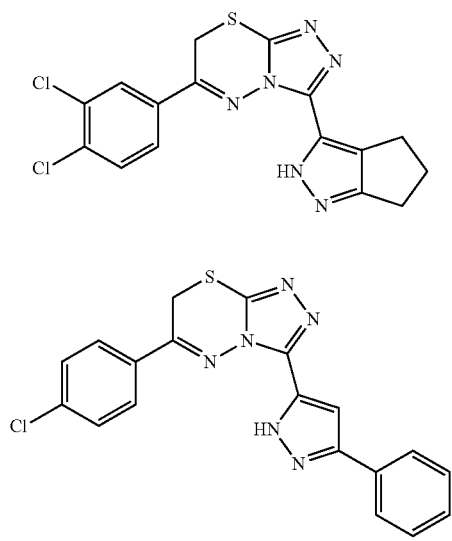

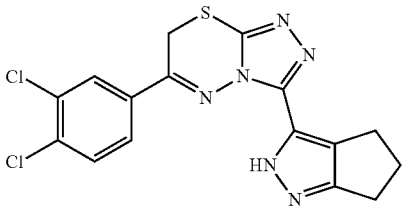 [SMILES: Clc1ccc(C2=Nn3c(nnc3-c3[nH]nc4c3CCC4)SC2)cc1Cl]

1a

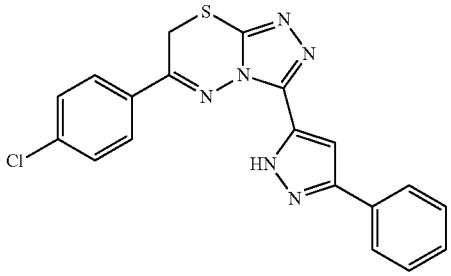 [SMILES: Clc1ccc(C2=Nn3c(nnc3-c3cc(-c4ccccc4)n[nH]3)SC2)cc1]

2b

| 1a | | 2b |
|---|---|---|
| 6.8 ± 3.7 | STAT3 IC$_{50}$ (μM) | 9.6±7.8 |
| >50 | STAT1 IC$_{50}$ (μM) | >50 |
| 14-26 | GI$_{50}$ HNSCC[a] (μM) | 27-44 |
| 391.2 | MW | 392.8 |
| 3.2 | cLogP | 3.7 |
| 1/4 | HBD/HBA | 1/4 |
| 71.7 | tPSA | 71.7 |
| 0.29 | LE | 0.26 |

[a]Cell lines 686LN, FADU, CAL33, OSC19

Example 6

Comparative STAT3 vs. STAT1 Activity

Compounds 1a to 13b were synthesized according to the following synthetic scheme. STAT3 and STAT1 activities of triazolothiadiazines were then measured, and are reported in the following table.

Scheme 1.

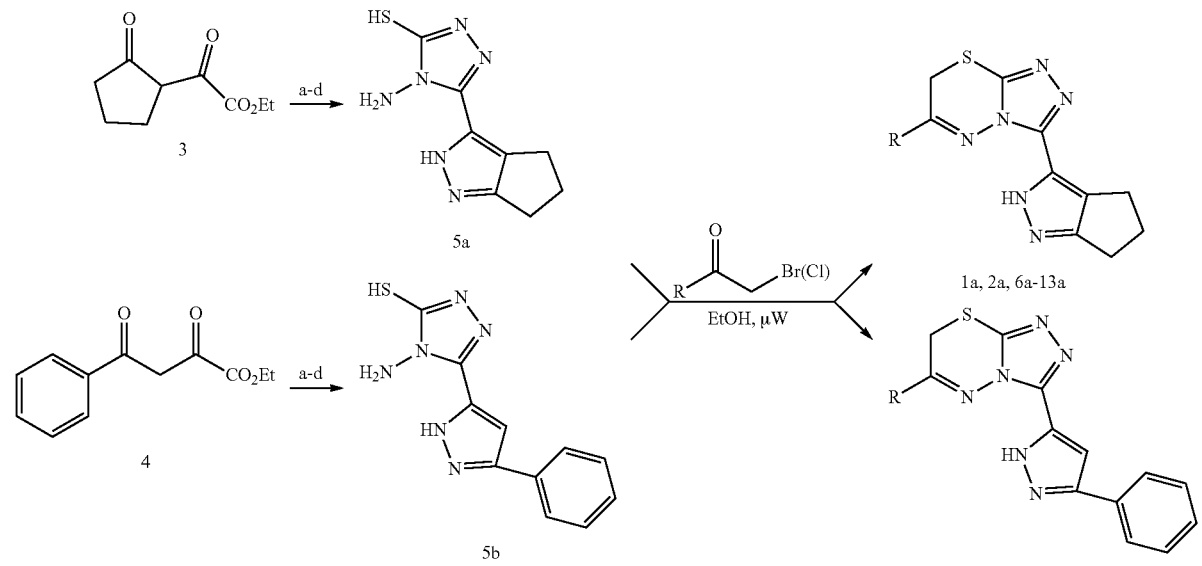

(a) hydrazine hydrate, AcOH (37-99%); (b) hydrazine hydrate, EtOH (66-96%); (c) CS$_2$, KOH, EtOH; (d) hydrazine hydrate, EtOH (20-90% over 2 steps).

TABLE 4

| R | Cmpd # | STAT3 IC$_{50}$ (µM) | STAT1 IC$_{50}$ (µM) |
|---|---|---|---|
| 3,4-dichloro-Ph | 1a | 6.8±3.7 | >50 |
| | 1b | 31.2±20.0 | >50 |
| 4-Cl-Ph | 2a | 26.8±22.3 | >50 |
| | 2b | 9.6±7.8 | >50 |
| 3-Cl-Ph | 6a | 21.2±5.9 | >50 |
| | 6b | 5.6±4.0 | 45.9±8.3 |
| Ph | 7a | 21.2±23.5 | >50 |
| | 7b | 27.0±7.4 | >50 |
| 4-MeO-Ph | 8a | 17.9±22.9 | 40.6±7.5 |
| | 8b | 3.7±2.5 | >50 |
| 4-pyridyl | 9a | >50 | >50 |
| | 9b | >50 | >50 |
| 5-Cl-thien-2-yl | 10a | 11.0±5.5 | >50 |
| | 10b | >50 | >50 |
| H—* | 11a | >50 | >50 |
| | 11b | >50 | >50 |
| Me—* | 12a | >50 | >50 |
| | 12b | >50 | >50 |
| cyclohexyl | 13a | >30 | >50 |
| | 13b | >50 | >50 |

Example 7

Preparation and Analysis of α-Substituted Analogs of the Thioether Moiety

Compounds of the following scheme were prepared according to the methods described herein. The activity of the compounds were compared and summarized in the following table.

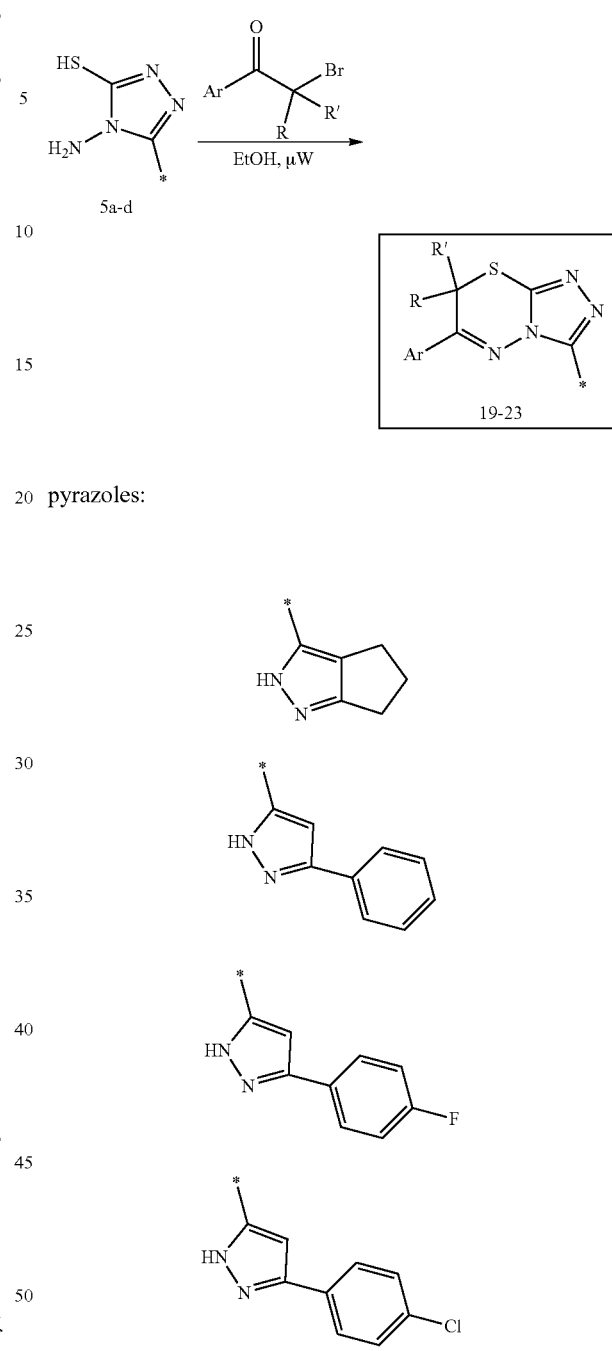

pyrazoles:

TABLE 5

| Cmpd # | Pyrazole series | Ar | R/R' | STAT3 IC$_{50}$ (µM) | STAT1 IC$_{50}$ (µM) | CAL33 GI$_{50}$ (µM) |
|---|---|---|---|---|---|---|
| 19 | a | 3,4-dichloro-Ph | Me/H | 8.2 ± 2.2 | >50 | 1.9 ± 1.2 |
| 20 | a | 4-OMe-Ph | Me/H | 9.1* | >50 | 0.2* |
| 21 | b | Ph | Me/H | 3.4* | 15* | 34.1 ± 8.7 |
| 22 | c | Ph | Me/H | 3.8 ± 0.8 | >30 | 36.3 ± 9.7 |
| 23 | c | 4-OMe-Ph | Me/H | 4.2* | >30* | 29.5 ± 6.5 |
| 24 | d | 4-OMe-Ph | Me/H | 11.4 ± 10.4 | 29.5* | 2.2 ± 0.3 |
| 24 (ent-1) | d | 4-OMe-Ph | Me/H | 5.72* | NT | 2.7* |

TABLE 5-continued

| Cmpd # | Pyrazole series | Ar | R/R' | STAT3 IC$_{50}$ (μM) | STAT1 IC$_{50}$ (μM) | CAL33 GI$_{50}$ (μM) |
|---|---|---|---|---|---|---|
| 24 (ent-2) | d | 4-OMe-Ph | Me/H | 17.3* | NT | 21.8* |
| 25 | a | 3,4-dichloro-Ph | iPr/H | 4.4* | >50 | 8.2* |
| 26 | a | 4-OMe-Ph | iPr/H | 2.2 ± 1.2 | >50 | 0.4 ± 0.1 |
| 27 | a | 3,4-dichloro-Ph | iBu/H | 4.1* | >50 | 3.5 ± 1.5 |
| 28 | b | 4-OMe-Ph | iBu/H | 5.1* | >50 | 0.5* |
| 29 | a | 3,4-dichloro-Ph | Bn/H | 7.5* | >50 | 3.3* |
| 30 | b | 4-OMe-Ph | (CH$_2$)$_2$NH$_2$/H | >20 | NT | 2.5* |
| 31 | b | 4-OMe-Ph | (CH$_2$)$_2$OMe/H | >50 | NT | 0.04* |
| 32 | a | 3,4-dichloro-Ph | Me/Me | 18.6* | >50 | >50* |

The Growth inhibition on HNSCC cell lines were then measured for compounds 20, 21 and 24.

TABLE 6

|  | 20 | 21 | 24 |
|---|---|---|---|
| 686LN GI$_{50}$ (μM) | 0.88* | 32.2* | 17.4* |
| CAL33 GI$_{50}$ (μM) | 0.18* | 34.1* | 2.2* |
| FADU GI$_{50}$ (μM) | 1.3* | 32.7* | 8.4* |
| OSC19 GI$_{50}$ (μM) | 3.1* | 31.3* | 14.9* |

(*average of 2 experiments)

The above examples are given to illustrate the present invention. It should be understood, however, that the spirit and scope of the invention is not to be limited to the specific conditions or details described in these examples. All publicly available documents referenced herein, including but not limited to U.S. patents, are specifically incorporated by reference.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A compound represented by the following formula:

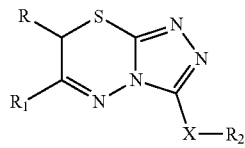

wherein:
R is selected from the group consisting of a C$_1$-C$_6$ alkyl or aryl, optionally substituted by one or more selected from the group consisting of OR', NR'R'',

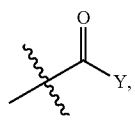

and an optionally substituted phenyl, wherein
(1) R' and R'' are each independently selected from —H, C$_1$-C$_6$ alkyl and C$_1$-C$_6$ alkyl substituted by one or more fluoro groups, and when R' and R'' are each alkyl they may form a ring, (2) Y is selected from C$_1$-C$_6$ alkyl, —OR', and —NR'R'', wherein when the optionally substituted phenyl contains a substituent, the substituent is selected from —OR', —NR'R'', and

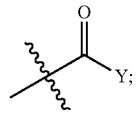

R$_1$ is

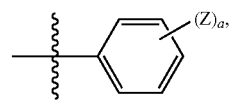

wherein
(1) each Z is independently selected from halogen, C$_1$-C$_6$ alkyl, C$_1$-C$_6$ alkyl substituted by one or more fluoro groups, —OR', —NR'R'',

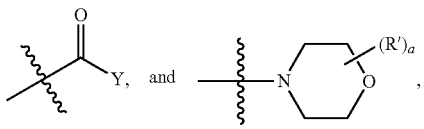

(2) a is an integer of 0 to 4,
(3) Y' is selected from C$_1$-C$_6$ alkyl, C$_1$-C$_6$ alkyl substituted by one or more fluoro groups, —OR', and —NR'R'', wherein R and R$_1$ may form a ring;
X is

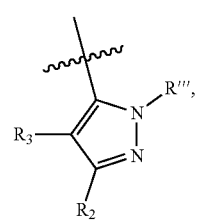

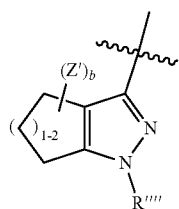

wherein $R_2$ is absent, or

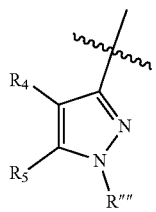

wherein $R_2$ is absent, wherein
(1) $R_2$ is phenyl optionally substituted by one or more halogen and $R_3$ is hydrogen or a halogen, or $R_2$ and $R_3$ form a 5 or 6-membered ring comprising sp$^3$ carbon atoms, and optionally one heteroatom selected from S, NR* and O, wherein R* is H, $C_1$-$C_6$ alkyl or benzyl,
(2) $R_5$ is phenyl optionally substituted by one or more halogen and $R_4$ is hydrogen or a halogen, or $R_5$ and $R_4$ form a 5 or 6-membered ring comprising carbon atoms, and optionally one heteroatom selected from S, NR* and O, wherein R* is H, $C_1$-$C_6$ alkyl or benzyl,
(3) Z' is halogen, benzyl, $C_1$-$C_6$ alkyl, and $C_1$-$C_6$ alkyl substituted by one or more fluoro groups,
(4) b is an integer from 0 to 4,
(5) R''' is hydrogen, $C_1$-$C_6$ alkyl, benzyl,

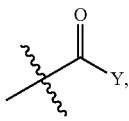

wherein the benzyl may be substituted by one or more halogen, $C_1$-$C_6$ alkyl, $C_1$-$C_6$ alkyl substituted by one or more fluoro groups, or —OR',
(6) R''' is hydrogen, $C_1$-$C_6$ alkyl, benzyl, or

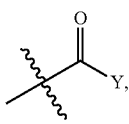

wherein the benzyl may be substituted by one or more halogen, $C_1$-$C_6$ alkyl, $C_1$-$C_6$ alkyl substituted by one or more fluoro groups or —OR',
or a pharmaceutically acceptable solvate or salt thereof, and
wherein when R and $R_1$ are both unsubstituted phenyl, then $R_2$ cannot be unsubstituted phenyl.

2. The compound of claim 1, wherein R is a $C_1$-$C_6$ alkyl or a benzyl.

3. The compound of claim 1, wherein R and $R_1$ form a 5 or 6 membered ring that is optionally substituted by one or more selected from the group consisting of —OR', —NR'R'',

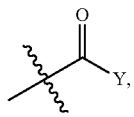

and an optionally substituted phenyl.

4. The compound of claim 1, wherein for $R_1$, a is 1 or 2, and Z is independently selected from fluoro, chloro, methyl, methoxy, and trifluoromethyl.

5. The compound of claim 1, wherein X is

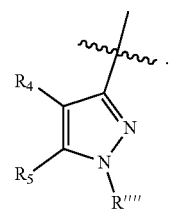

wherein $R_2$ is absent.

6. The compound of claim 1, wherein X is

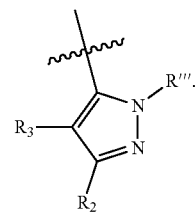

7. The compound of claim 1, wherein $R_2$ and $R_3$ form a 5 or 6-membered ring comprising sp$^a$ carbon atoms, and optionally one heteroatom selected from S, NR* and O.

8. A compound selected from the group consisting of:

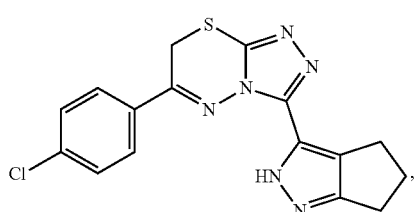

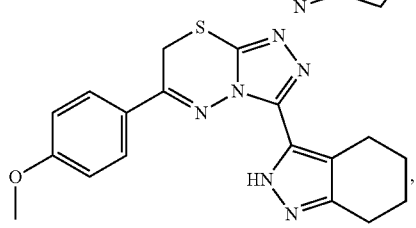

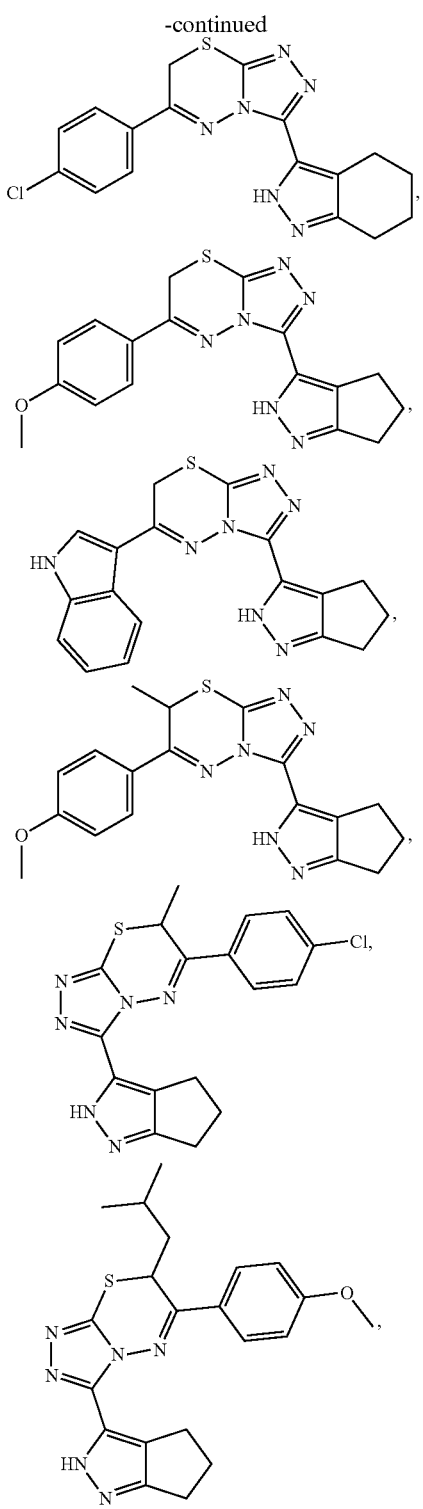

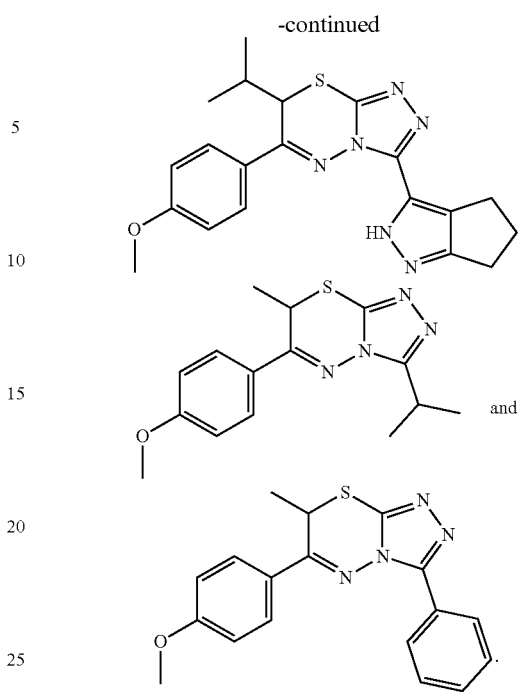

9. A pharmaceutical formulation comprising a compound according to claim 1, and a pharmaceutically acceptable excipient.

10. A method of treating Squamous Cell Carcinoma in a patient in need thereof, comprising administering to the patient a therapeutically effective amount of a pharmaceutical formulation according to claim 9.

11. The method of claim 10, wherein the Squamous Cell Carcinoma is located in the head and/or neck.

12. A method of treating a cancer with hyper-activated STAT3 in a patient in need thereof, comprising administering to the patient a therapeutically effective amount of a pharmaceutical formulation according to claim 9.

13. A method of inhibition of STAT3 comprising contacting STAT3 with a pharmaceutical formulation according to claim 9.

14. A method of selectively inhibiting STAT3 in the presence of STAT1 comprising contacting STAT3 with a pharmaceutical formulation according to claim 9.

15. A method of treatment of a STAT3-mediated disease comprising the administration of a therapeutically effective amount of the pharmaceutical formulation according to claim 9 to a patient in need thereof.

16. The method as recited in claim 15 wherein the disease is cancer.

17. The method as recited in claim 16 wherein the cancer is Squamous Cell Carcinoma.

18. The method of claim 10, wherein the compound or pharmaceutical formulation is administered orally.

* * * * *